United States Patent
Bitler et al.

(10) Patent No.: US 6,379,882 B1
(45) Date of Patent: Apr. 30, 2002

(54) METHOD FOR SELECTING COMPOUNDS FOR TREATING ISCHEMIA-RELATED CELLULAR DAMAGE

(75) Inventors: Catherine M. Bitler; Anke Meyer-Franke; Paul Wood, all of Menlo Park, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/393,137

(22) Filed: Sep. 10, 1999

Related U.S. Application Data

(60) Provisional application No. 60/138,855, filed on Jun. 11, 1999, provisional application No. 60/137,618, filed on Jun. 4, 1999, and provisional application No. 60/100,241, filed on Sep. 14, 1998.

(51) Int. Cl.$^7$ .......................... C12Q 1/00; G01N 33/53; A61K 38/28; A61K 31/455

(52) U.S. Cl. ................................ 435/4; 435/6; 435/7.8; 514/3; 514/12; 514/13; 514/14; 514/21; 514/29; 514/35; 514/36; 514/37; 514/38; 514/46; 514/49; 530/399

(58) Field of Search ..................... 435/4, 6, 7.8; 514/29, 514/3, 12–19, 49, 35–38, 46, 21; 530/399

(56) References Cited

U.S. PATENT DOCUMENTS

| | | | |
|---|---|---|---|
| 5,051,403 A | | 9/1991 | Mijanich et al. |
| 5,395,822 A | * | 3/1995 | Izumi et al. .................... 514/3 |
| 5,401,755 A | * | 3/1995 | Rice et al. .................. 514/336 |
| 5,559,095 A | | 9/1996 | Mijanich et al. |
| 5,677,288 A | * | 10/1997 | Marangos ..................... 514/39 |
| 5,733,871 A | * | 3/1998 | Alps et al. ..................... 514/12 |
| 5,739,529 A | * | 4/1998 | Adams et al. ................. 514/46 |
| 5,801,160 A | * | 9/1998 | Sandage et al. ............... 514/49 |
| 6,060,238 A | * | 5/2000 | Dixit ............................. 435/6 |

OTHER PUBLICATIONS

Allen, R. T., et al., "Mechanisms controlling cellular suicide: role of Bcl–2 and caspases," *CMLS Cellular and Molecular Life Science*, 54:(5)427–445 (1998).

Bähr, M., et al., "Perspectives on axonal regeneration in the mammalian CNS," *Trends in Neuroscience*, 7(11):473–479 (1994).

Bähr, M., "Adult Rat Retinal Glia in Vitro: Effects of in vitro Crush–Activation on Glia Proliferation and Permissiveness for Regenerating Retinal Ganglion Cell Axons," *Experimental Neurology*, 111:65–73 (1991).

Barres, B.A., et al., "Cell Death and Control of Cell Survival in the Oligodentrocyte Lineage," *Cell*, 70:31–46 (1992).

Barres, B.A., et al., "Immunological, Morphological, and Electrophysiological Variation Among Retinal Ganglion Cells Purified by Panning," *Neuron*, 1:791–803 (1988).

Barres, B.A., et al., "Multiple extracellular signals are required for long–term oligodendrocyte survival," *Development*, 118:283–285 (1993).

Batistatou, A., et al., "Internucleosomal DNA Cleavage and Neuronal Cell Survival/Death," *The Journal of Cell Biology*, 122(3):523–532 (1993).

Bean, B.P., "Classes of Calcium Channels in Vertebrate Cells," *Annual Review of Physiology*, 51:367–384 (1989).

Berkelaar, M., et al., "Axotomy Results in Delayed Death and Apoptosis of Retinal Ganglion Cells in Adult Rats," *The Journal of Neurosciences*, 14(7):4368–4374 (1994).

Bittigau, P., et al., "Glutamate in Neurologic Diseases," *J. Child Neurol.*, 12:471–485 (1997).

Bonfoco, E., et al., "Apoptosis and necrosis: Two distinct events induced, respectively, by mild and intense insults with N–methyl–D–aspartate or nitric oxide/superoxide in cortical cell cultures," *Proc. Nat Acad. Sci. USA*, 92:7162–7166 (1995).

Buchan, A.M., et al., "A Selective N–Type $Ca^{2+}$–Calcium Blocker Prevents Cal Injury 24 h Following Severe Forebrain Ischemia and Reduces Infarction Following Focal Ischemia," *Journal of Cerebral Blood Flow Metabolism*, 14(6):903–910 (1994).

Busciglio, J., et al., "Apoptosis and increased generation of reactive oxygen species in Down's syndrome neurons in vitro," *Nature*, 378:776–779 (1995).

Chen, Q., et al., "Fenamates protect neurons against ischemic and excitotoxic injury in chick embryo retina," *Neuroscience Letters*, 242(3):163–166 (1998).

Cohen–Cory, S. et al., "BDNF in the Development of the Visual System of Xenopus," *Neuron*, 12:747–61 (1994).

Evans, R.H., et al., "The Effects of a Series of ω–Phosphonic α–Carboxylic Amino Acids on Electrically Evoked and Excitant Amino Acid–Induced Responses in Isolated Spinal Cord Preparations," *Br. J. Pharmacol.*, 75(1):65–75 (1982).

Finlay, B.L., "Cell Death and the Creation of Regional Differences in Neuronal Numbers," *Journal of Neurobiology*, 23(9):1159–1171 (1992).

Fraser, A., et al., "Biochemistry of cell death," *Current Opinion in Neurobiology*, 6:71–80 (1996), Garcia–Valenzuela, E., et al., "Programmed Cell Death of Retinal Ganglion Cells During Experimental Glaucoma," *Exp. Eye Res.*, 61(1):33–44 (1995).

(List continued on next page.)

Primary Examiner—Lynette R. F. Smith
Assistant Examiner—Padma Baskar
(74) Attorney, Agent, or Firm—Carol A. Stratford

(57) ABSTRACT

A method of screening for and treating subjects with a therapeutically effective amount of a compound that is effective in reducing cellular damage related to an ischemic condition, such as stroke or glaucoma. Test compounds are selected and therapeutically effective amount determined based on the relative efficacy of test compounds in preventing cell death in primary cultures of excitable cells, such as retinal ganglion cells, in vitro.

13 Claims, 12 Drawing Sheets

OTHER PUBLICATIONS

Ghosh, A., et al., "Requirement for BDNF in Activity–Dependent Survival of Cortical Neurons," *Science*, 263:1618–1623 (1994).

Goldberg, Y.P., et al., "Cleavage of huntingtin by apopain, a proapoptotic cysteine protease, is modulated by the polyglutamine tract," *Nat. Genetic*, 13:442–449 (1996).

Greenlund, L.J.S., et al., "Superoxide Dismutase Delays Neuronal Apoptosis: A Role for Reactive Oxygen Species in Programmed Neuronal Death," *Neuron*, 14:303–315 (1995).

Gwag, B.J., et al., "Blockade of Glutamate Receptors Unmasks Neuronal Apoptosis After Oxygen–Glucose Deprivation In Vitro," *Neuroscience*, 68(3):615–619 (1995).

Hinton, D.R., et al., "Apoptosis in Surgically Excised Choroidal Neovascular Membranes in Age–Related Macular Degeneration," *Arch. Ophthalmol.*, 116:203–209 (1998).

Hsu, C.Y., et al., "A Stroke Model Designed for Preclinical Trial," *Cerebral Ischemia and Resuscitation*, 3:47–59 (1990).

Ilschner, S.U., "Fragmentation of DNA in the Retina of Chicken Embryos Coincides with Retinal Ganglion Cell Death," *Biochem. Biophys. Res. Commun.*, 183(3):1056–1061 (1992).

Isenmann, S., et al., "Up–regulation of Bax Protein in Degenerating Retinal Ganglion Cells Precedes Apoptotic Cell Death after Optic Nerve Lesion in the Rat," *European Journal of Neuroscience*, 9:1763–1772 (1997).

Kim, R.J., et al., "Relationship of Elevated $^{23}$Na Magnetic Resonance Image Intensity of Infarct Size After Acute Reperfused Myocardial Infarction," *Science*, 277:373–376 (1997).

Kim, T., et al., "Alternative Cleavage of Alzheimer–Associated Presenilins During Apoptosis by a Caspase–3 Family Protease," *Science*, 277:373–176 (1997).

Kirino, T., "Delayed Neuronal Death in the Gerbil Hippocampus Following Ischemia," *Brain Research*, 239:57–69 (1982).

Kitano, S. et al., "Hypoxic and Excitotoxic Damage to Cultured Rat Retinal Ganglion Cells," *Experimental Eye Research*, vol. 63(1):105–112 (1993).

Kral, T., et al., "Role of NMDA receptors and voltage–activated calcium channels in an in vitro model of cerebral ischemia." *Brain Research*, 612:278–288 (1993).

Kristiàn, T. et al., "Calcium in Ischemic Cell Death," *Stroke*, 29:705–718 (1998).

Lagréze, W.A., et al., "Memantine Is Neuroprotective in a Rat Model of Pressure–Induced Retinal Ischemica," *IOVS. Sci.*, 39:1063–1066 (1998).

Laquis, S., et al., "The patterns of retinal ganglion cell death in hypertensive eyes," *Brain Research*, 784:100–104 (1998).

Lazdins, J.K., et al., "Membrane Tumor Necrosis Factor (TNF) Induced Cooperative Signaling of TNFR60 and TNFR80 Favors Induction of Cell Death Rather Than Virus Production in HIV–infected T Cells," *J. Exp. Med.*, 185:81–90 (1997).

Lehmann, J., et al., "CGS 19755 is a potent and competitive antagonist at NMDA–type receptors," *Eur. J. Pharmacol.*, 154:89–93 (1988).

Lipton, S.A., et al., "Excitatory Amino Acids As A Final Common Pathway For Neurologic Disorders," *N. Eng. J. Med.*, 330(9):613–622 (1994).

Liston, P., et al., "Suppresion of apoptosis in mammalian cells by NAIP and a related family of IAP genes," *Nature*, 379:349–353 (1996).

MacManus, J.P., et al., "Global ischemia can cause DNA fragmentation indicative of apoptosis in rat brain," *Neuroscience Letters*, 164:89–92 (1993).

Marte, B.M., et al., "PKB/Akt: connecting phosphoinositide 3–kinase to cell survival and beyond," *Trends Biochem. Sci.*, 9:355–358 (1997)

Meyer–Franke, A., et al., "Characterization of the Signaling Interactions That Promote the Survival and Growth of Developing Retinal Ganglion Cells in Culture," *Neuron*, 15:805–819 (1995).

Morrison, J.C., et al., "A Rat Model of Chronic Pressure––induced Optic Nerve Damage," *Exp. Eye Res.*, 64:85–96 (1997).

Mosmann, T., "Rapid Colorimetric Assay for Cellular Growth and Survival: Application to Proliferation and Cytotoxicity Assays," *J. Immunol. Meth.*, 65:55–63 (1983).

Nickells, R.W., "Retinal Ganglion Cell Death in Glaucoma: The How, the Why, and the Maybe," *J. Glaucoma*, 5(5):345–356 (1996).

Oppenheim, R.W., et al., "Naturally Occuring and Induced Neuronal Death in the Chick Embryo in Vivo Requires Protein and RNA Synthesis: Evidence for the Role of Cell Death Genes," *Developmental Biology*, 138:104–113 (1990).

Pellegrini–Giamietro, D.E., et al., "Excitatory Amino Acid Release from Rat Hippocampal Slices as a Consequence of Free–Radical Formation," *Journal of Neurochemistry*, 51:1960–1963 (1988).

Perez–Pinzon, M.A., "SNX–111, a novel, presynaptic N–type calcium channel antogonist, is neuroprotective against focal cerebral ischemia in rabbits," *Journal of Neurological Sciencs*, 153(1):25–31 (1997).

Peter, M.E., et al., "Advances in appoptosis research," *Proc. Nat. Acad. Sci.*, 94:12736–12737 (1997).

Pislaru, S.V., et al., "Noninvasive Measurements of Infarct Size After Thrombolysis With a Necrosis–Avid MRI Contrast Agent," *Circulation*, 99(5):690–696 (1999).

Pulsinelli, W.A., et al., "A New Model of Bilateral Hemispheric Ischemia in the Unanesthetized Rat," *Stroke*, 10:267–272 (1979).

Raff, M.C., et al., "Programmed cell death and the control of cell survival," *Philos. Trans. Royal Soc. Lond. B. Biol. Sci.*, 354(1313):265–268 (1994).

Raff, M.C., "Cell Death Genes: Drosophila Enters the Field," *Science*, 264(5159):668–669 (1994).

Romano, C., et al., "Excitotoxic Neurodegeneration Induced by Deprivation of Oxygen and Glucose in Isolated Retina," *Investigative Ophthalmology & Visual Science*, 39(2):416–423 (1998).

Schaden, H., et al., "GAP–43 Immunoreactivity and Axon Regeneration in Retinal Ganglion Cells of the Rat," *Journal of Neurobiology*, 25:1570–1578 (1994).

Schwartz, L.M., et al., "Do all programmed cell deaths occur via apoptosis?," *Proc. Nat. Acad. Sci. USA*, 90:980–984 (1993).

Schwartz, P.J., "Do Animal Models have Clinical Value?," *Am. J. Cardiol.*, 81(6A): 14D–20D (1999).

Strasser, U., et al., "Quantitive Measurement of neuronal degeneration in organotypic hippocampal cultures after combined oxygen/glucose deprivation," *Journal of Neuroscience Methods*, 57:177–186 (1995).

Sucher, N.J., et al., "N–methyl–D–aspartate Antagonists Prevent Kainate Neurotoxicity in Rat Retinal Ganglion Cells in vitro," *The Journal of Neuroscience*, 11(4):966–971 (1991).

Takizawa, S., et al., "A Selective N–Type Calcium Channel Antagonist Reduces Extracellular Glutamate Release and Infarct Volume in Focal Cerebral Ischemia," *J. Cereb. Blood Flow Metab.*, 4:611–618 (1995).

Tamura, A., et al., "Focal Cerebral Ischaemia in the Rat: 1. Description of Technique and Early Neuropathological Consequences Following Middle Cerebral Artery Occlusion," *Journal Cereb. Blood Flow Metab.*, 1:53 (1981).

Toner, C.C., et al., "Characteristics of the NMDA receptor modulating hypoxia/hypoglycaemia–induced rat striatal dopamine release in vitro," *Eur. J. Pharmocol.*, 340:133–143 (1997).

Tsien, R.W., et al., "Multiple types of neuronal calcium channels and their selective modulation," *TINS*, 11(10):431–438 (1988).

Valentino, K., et al., "A selective N–type calcium channel antagonist protects against neuronal loss after global cerebral ischemia," *Proc. Natl. Acad. Sci.*, 90:7894–7897 (1993).

Vermes, I., et al., "A novel assay for apoptosis Flow cyotmetric detection of phosphatidylserine expression on early apoptotic cells using fluorescein labelled Annexin V," *J. Immunol. Meth.*, 184:39–51 (1995).

Verweij, B.H., et al., "Mitochrondrial dysfunction after experimental and human brain injury and its possible reversal with a selective N–type calcium channel antagonist (SNX–111)," *Neurol. Res.*, 19:334–339 (1997).

Villegas–Perez, M., et al., "Rapid and Protracted Phases of Retinal Ganglion Cell Loss Follow Axotomy in the Optic Nerve of Adult Rats," *Journal of Neurobiology*, 24:23–36 (1993).

Vitale, M., et al., "Differential kinetics of propidium iodide uptake in apoptotic and necrotic thymocytes," *Histochemistry*, 100:223–229 (1993).

Walton, M., et al., "Annexin V labels apoptotic neurons following hypoxia–ischemia," *Neuroreport*, 3(18):3871–3875 (1997).

Wyllie, A.H., "Apoptosis (The 1992 Frank Rose Memorial Lecture)," *Br. J. Cancer*, 67(29):205–208 (1993).

Wyllie, A.H., "Apoptosis: an overview," *Br. Med. Bull,*, 53(3):451–465 (1997).

Wyllie, A.H., "The Genetic Regulation of apoptosis," *Curr. Opin. Genet. Dev.*, 5(1):97–104 (1995).

Wyllie, A.H., et al., "Chromatin Cleavage in Apoptosis: Association with Condensed Chromatin Morphology and Dependence on Macromolecular Syntheses," *J. Pathol.*, 142:67–77 (1984).

Yamamoto, H., et al., "Effects of 2–amino–7–phosphonoheptanoic acid, melatonin or $N^G$–nitro–L–argine on cyanide or N–methyl–D–aspartate–induced neurotoxicity in rat cortical cells," *Toxicology Letters*, 94:13–18 (1998).

Zhao, Q., et al., "Hyperthermia complicates middle cerebral artery occlusion induced by an intraluminal filament," *Brain Research*, 649:253–259 (1994).

Zornow, M.H., et al., "Neuroprotective Properties of Calcium–Channel Blockers," *New Horizons*, 1:107–114 (1996).

Newell et al; Brain Research 675; 38–44, 1995.*

Nath et al; Journal of Neurochemistry; 71; 186–195, 1998.*

R&D System; Apoptosis Detection Kit; Cat.No.KNX50, 1995.*

* cited by examiner

METHOD FOR SELECTING COMPOUNDS FOR TREATING ISCHEMIA-RELATED CELLULAR DAMAGE

This application claims the benefit of U.S. Provisional Application Nos. 60/100,241 filed Sep. 14, 1998, 60/137,618, filed Jun. 4, 1999 and 60/138,855, filed Jun. 11, 1999, all of which are hereby incorporated herein by reference in their entireties.

FIELD OF THE INVENTION

The present invention relates to a method of screening compounds capable of reducing cellular damage associated with an ischemic condition, including stroke, glaucoma and other neurodegenerative diseases, as well as myocardial infarction, and to methods of treating patients who are susceptible to or who exhibit ischemia-related cellular damage.

BACKGROUND OF THE INVENTION

Ischemic injury to cells and tissues occurs as a result of a number of insults that result in decreased perfusion with oxygenated blood, e.g., cerebral ischemia ("stroke"), myocardial infarction and reperfusion injury (Walton, et al., *Neuroreport* 8(18):3871–3875 (1997); MacManus, et al., *Neurosci. Lett.* 164:389–92 (1993)). Two distinct patterns of pathologic cell death are generally associated with cellular ischemia: necrosis and apoptotic cell death. As described in greater detail in Section II, below, each of these types of cellular death are characterized by distinct, recognizable morphological and biochemical characteristics. Numerous diseases have been associated with faulty regulation of apoptosis including, e.g., neurodegenerative conditions, AIDS and vascular disease. [Allen, et al., *Cell Mol. Life Sci.* 54(5):427–445 (1998)].

Ischemic damage to the central nervous system (CNS) may result from either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors. Both global and focal ischemic conditions have the potential for producing widespread neuronal damage, even if the ischemic condition is transient.

Animal models have been established that mimic the symptoms of both global and focal cerebral ischemia, most notably, the gerbil model of global ischemia produced by transient occlusion of carotid arteries of the neck. [Kirino, *Brain Res.* 239:57–69 (1982)], the rat four-vessel occlusion model for ischemia [Pulsinelli, et al., *Stroke* 10:267–272 (1979)], the MCAO microfilament of focal ischemia [Tamura, et al., *Journal Cereb. Blood Flow Metab.* 1:53 (1981)], and a rat model for glaucoma [Isenmann, et al., *Eur. J. Neurosci.* 9:1763–1772 (1997)]. Although animal models are important sources of information as to which candidate therapeutics are likely to be efficacious in mammals, they are costly, time consuming and not amenable to screening large numbers of compounds.

There exists a need for an in vitro screening system effective to discriminate between the large number of potential therapeutic agents that are available for treatment of ischemia- and apoptosis-related disorders. The present invention provides reliable, reproducible predictor assays that are adaptable to screening large numbers of test compounds in parallel. Such in vitro assays facilitate selection of candidate compounds, which can then be tested in relevant animal models to determine if they are suitable for administration to human patients. The present invention also provides compounds and methods of treatment based on performance of candidate compounds in such in vitro assays.

SUMMARY OF THE INVENTION

The present invention is directed to the discovery of in vitro methods for selection of candidate therapeutic agents for in vivo treatment of disorders having as their underlying etiology, ischemia-related cellular damage or death. Such disorders include, but are not limited to ischemia, glaucoma and other neurodegenerative diseases, as well as cardiac injury associated with myocardial infarction. While such disorders are usually characterized by apoptotic cell death, apoptosis or necrosis may or may not be involved.

The present invention is also directed to the use of such in vitro methods for determining a therapeutically effective amount of a given candidate therapeutic agent for the in vivo treatment of such disorders in a subject.

The present invention is based, in part, on the discovery of a method for selecting compounds which are candidates for treatment of ischemia-related cellular damage. The invention includes a method for evaluating the relative efficacy of such compounds based on decreased cell death in oxygen/glucose-deprived excitable cells in culture, exemplified by neuronal cells, such as retinal ganglion cells ("RGCs") or myocardial cells, such as myocytes, in in vitro primary cultures. In a preferred embodiment, such cells are prepared in culture to be at least 80% and preferably at least 90%, and more preferably 99% homogeneous with respect to other cells in the culture or cell population employed in the assay.

The present invention is also based on the discovery of a method for selecting test compounds that are candidate cellular protective agents for treatment of myocardial infarction, glaucoma and other neurodegenerative diseases. In this aspect, the invention includes a method for evaluating the relative efficacy of such test compounds based on decreased cell death in growth factor-deprived or oxygen/glucose and growth factor-deprived retinal ganglion cells in vitro.

In the assays of the present invention, cell death may be related to apoptosis or necrosis. Accordingly, the relative efficacy of test compounds for treatment of ischemia-related neuronal cell damage, including glaucoma and other neurodegenerative diseases may be evaluated in the retinal ganglion cell models of the present invention using endpoints indicative of apoptotic and/or necrotic cell death. Likewise, the relative efficacy of such test compounds for treatment of myocardial cell damage, such as caused by myocardial infarction, may be evaluated in myocyte cell models of the present invention.

In a related aspect, the present invention provides a method for reducing cellular damage related to an ischemic condition by administering to a subject, a therapeutically effective amount of one or more test compounds as determined by the relative efficacy of the one or more test compounds in reducing cell death due to the ischemic condition in an in vitro assay of oxygen/glucose-deprived excitable cells, as exemplified by retinal ganglion cells or myocytes. In the present invention, the in vitro cell death of oxygen/glucose-deprived retinal ganglion cells may occur by an apoptotic or necrotic mechanism.

In another aspect, the present invention provides a method for reducing cellular damage related to myocardial infarction, glaucoma or another neurodegenerative disease by administering to a subject, a therapeutically effective amount of a test compound as determined by the relative efficacy of the test compound in reducing cell death due to the ischemic condition in an in vitro assay of growth factor or oxygen/glucose and growth factor-deprived retinal ganglion cells. In the present invention, the in vitro cell death of growth factor or oxygen/glucose and growth factor-deprived retinal ganglion cells generally occurs by an apoptotic or necrotic mechanism.

These and other objects and features of the invention will become more fully apparent when the following detailed description of the invention is read in conjunction with the accompanying drawings.

DETAILED DESCRIPTION OF THE INVENTION

I. Definitions

Figure 1:
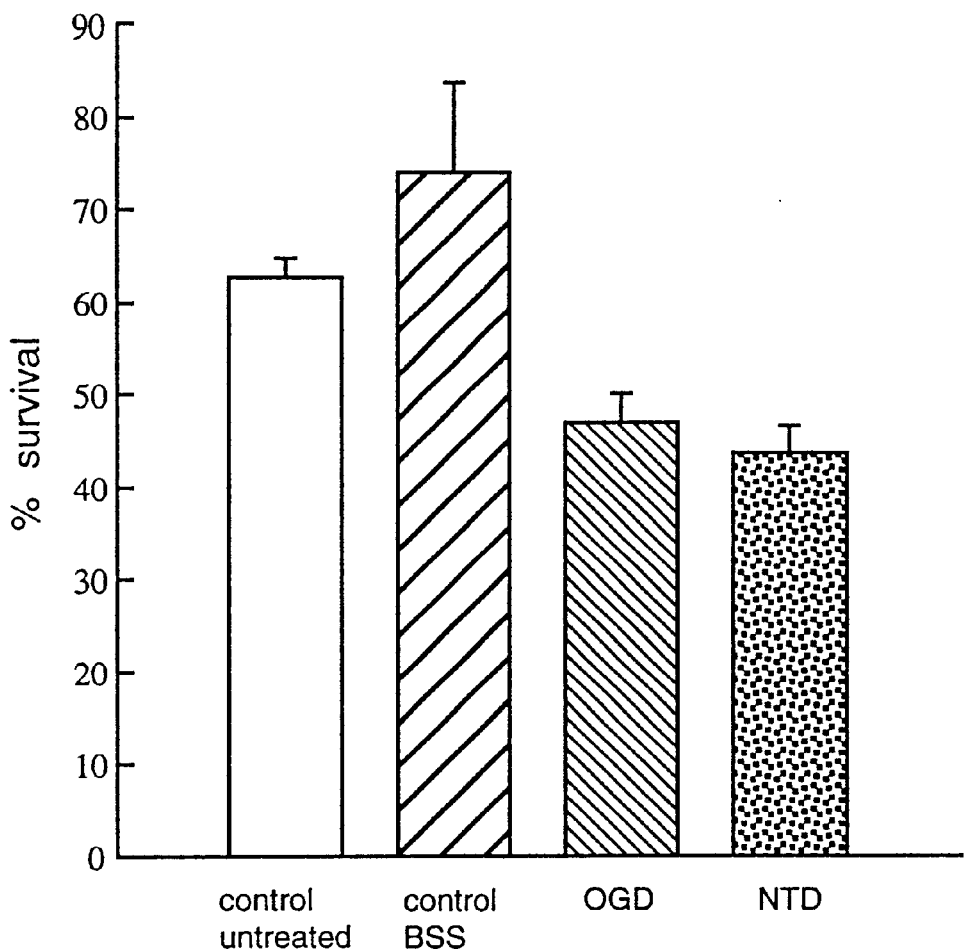
FIG. 1 shows the percentage of cell death of retinal ganglion cells 24 hours after oxygen/glucose deprivation (OGD) as determined by FITC-annexin assay (ApoAlert Kit, Clontech, Palo Alto, Calif.).

The term "ischemia" refers to a condition in which a cell, tissue or organ experiences a lack of oxygen to inadequate perfusion, e.g., reduced blood flow.

The term "ischemia-related cellular damage" is used generically to indicate a condition wherein cellular damage or death occurs consequent to reduced oxygenation of cells in a specific region, such as occurs as a result of reduced blood flow to the region. Examples of ischemia-related cellular damage include damage and death to myocardial tissue which occurs as a result of reduced or interrupted blood flow to the myocardium and ischemia-related neuronal damage, as described below.

The term "ischemia-related neuronal damage" as used herein refers to damage resulting from conditions in which blood flow to a neuron-enriched region, such as the spinal cord or the entire brain ceases for a period of time (e.g. due to cardiac arrest) (global ischemia) or when a portion of the brain or spinal cord is deprived of its normal blood supply (focal ischemia).

"Ischemic challenge" or "oxygen/glucose deprivation" as used herein refers to culture of cells under hypoxic or anaerobic conditions in culture medium lacking glucose. Such in vitro oxygen/glucose deprivation is sufficient to produce cell death in at least 25% of OGD retinal ganglion cells.

A specific cell culture is "at least about X% pure" or "at least about X% homogeneous" when the named cells constitute at least about X% of the cells present in the culture dish. In this same context, the term "substantially pure" or "substantially homogeneous" indicates that the cells are at least about 75% pure or homogeneous with respect to other cell types.

"Growth factor deprivation" as used herein with reference to cultures of retinal ganglion cells refers to incubation of the cells in culture medium lacking added growth factors, e.g., brain-derived neurotrophic factor (BDNF), ciliary neurotrophic factor (CNTF), insulin-like growth factor-1 (IGF-1), insulin, and forskolin or any other growth factors that would support growth of the cells in defined medium under conditions wherein the growth factor deprivation is sufficient to produce cell death in at least 25% of the retinal ganglion cells cultured in growth factor-deficient medium.

The term "candidate compound" as used herein describes any molecule, e.g., protein, oligopeptide, small organic molecule, polysaccharide, polynucleotide, etc., with the capability of directly or indirectly reducing the percentage of cell death of retinal ganglion cells in culture when the cells are subjected to either an oxygen/glucose deprivation challenge and/or a growth factor deprivation challenge.

"Apoptotic cell death" or "programmed cell death" as used herein refers to any cell death that results from a complex cascade of cellular events that occur at specific stages of cellular differentiation and in response to specific stimuli. Apoptotic cell death is characterized by condensation of the cytoplasm and nucleus of dying cells, fragmentation of DNA, membrane blebbing and by the translocation of phosphatidylserine, a membrane phospholipid from the inner side of the plasma membrane to the outer side.

"Necrotic cell death" as used herein refers to cell death associated with a passive process involving loss of integrity of the plasma membrane and subsequent swelling, followed by lysis of the cell.

"Primary culture" of cells refers to a culture of started from cells, tissue, or organs taken directly from an organism and before the first subculture. Such cells are typically isolated from a primary tissue source, dissociated, and incubated in a suitable growth medium under cell culture conditions. Such cells may also undergo procedures to effect isolation of homogeneous cell types prior to or while in culture.

An "excitable cell" is a cell that is capable of generating an action potential in response to a chemical or electrical stimulus. Examples of excitable cells include neuronal cells, such as retinal ganglion cells, and myocardial cells, such as myocytes. Such cells are generally characterized by the presence of voltage- and or ligand-gated ion channels, such as calcium channels, potassium channels and sodium channels. For example, neuronal calcium channels generate both electrical and chemical signals when they open in response to membrane depolarization and allow calcium ions to flow down their electrochemical gradient.

By "calcium channel blocker" as used herein is meant a compound effective to interfere with the flow of $Ca^{++}$ ions down the electrochemical gradient of one or more calcium channels. The term "antagonist" is synonymous with the term "blocker" in this context.

N-methyl-D-aspartate (NMDA) receptors interact with glutamate, the primary excitatory neurotransmitter ("excitotoxin") in the brain. Overstimulation of the NMDA receptors opens $Ca^{2+}$ channels in the cell membrane.

By "NMDA receptor antagonist" as used herein is meant a compound effective to interfere with the overstimulation of NMDA receptors and thereby modulate the excitatory effect of such overstimulation.

By "neuroprotective agent" as used herein is meant a compound effective to reduce neuronal cell death, including the ability to inhibit the spread of neuronal damage from the initial site of injury. An additional criterion for a neuroprotective agent is a selective effect on neuronal cells, as opposed to more widespread effects on other cell types. Compounds selected by the in vitro screening methods of the present invention are thus predicted to be neuronal-cell specific, neuroprotective agents.

By "therapeutically effective amount" as used herein is meant a dose that reduces or eliminates cell death associated with ischemia. The exact dose will depend on the purpose of the treatment, and will be ascertainable by one skilled in the art using known techniques. As is known in the art, adjustments for compound degradation, systemic versus localized delivery, as well as the age, body weight, general health, sex, diet, time of administration, drug interaction and the severity of the condition may be necessary, and will be ascertainable with routine experimentation by those skilled in the art.

A "subject" for the purposes of the present invention includes humans and other animals, particularly mammals. Thus, the methods described herein are applicable to both human therapy and veterinary applications. Preferably, the patient is a mammal, and most preferably the patient is human.

II. Mechanisms of Cell Death in Ischemia and Targets for Drug Intervention

This section describes various theories of the etiologies of cell damage and death associated with ischemic cell damage. Assay methods in accordance with the present invention are not dependent on any particular theory or mechanism; this section serves as a guide to the types of compounds that might serve as test compounds leading to candidate compounds for treating ishemic cell damage.

A. Apoptotic Cell Death Associated with Ischemia

Two distinct patterns of pathologic cell death have been associated with ischemia. The first is consistent with necrosis, and manifests an early loss of membrane integrity, abnormal organellar morphology, cellular swelling, occurrence in foci, and lysosomal rupture. The second is consistent with apoptosis and occurs in scattered cells rather than in foci, features chromatin condensation, nuclear fragmentation, decrease in cellular volume, plasma membrane blebbing, morphological preservation of organellar structure and preservation of membrane integrity, budding off of cellular fragments, and retained lysosomal contents.

Apoptosis is a normal physiological process that results from a complex cascade of cellular events [Raff, et al., *Philos. Trans. R. Soc. Lond. B. Biol. Sci.* 354(1313):265–268 (1994); Raff, *Science* 264(5159):668–669 (1994); Wyllie, *Br. Med. Bull.* 53(3):451–465 (1997); Wyllie, *Curr. Opin. Genet. Dev.* 5(1):97–104 (1995); Wyllie, *Br. J. Cancer* 67(29):205–208 (1993)]. It is now believed that in many cases, apoptosis may be a "default" program that must be actively inhibited in healthy surviving cells. For example, in the developing vertebrate nervous system, approximately half the neurons generated in most neuronal populations die during the period when synapses are being formed between neurons and their targets. As mentioned above, however, apoptosis is also a predominant form of cell death that occurs as a consequence of cellular ischemia.

Morphologically, apoptotic cell death is characterized by condensation of the cytoplasm and nucleus of dying cells. Apoptosis is characterized by early breakdown of DNA that can be visualized as internucleosomal fragmentation [Schwartz, et al., *Proc. Nat. Acad. Sci.* 90:980–984 (1993], and is known to be the pathway that ganglion cells and other neurons follow during developmental cell death [Finlay, *J. Neurobiol.* 23:1159–1171 (1992); Ilschner and Waring, *Biochem. Biophys. Res. Commun.* 183:1056–1061 (1992); Oppenheim, et al., *Devel. Biol.* 138:104–113 (1990)]. When viewed under a light microscope, the condensing nuclei are described as pyknotic. Ultrastructurally, the chromatin becomes electron dense, begins to accumulate at the inner surface of the nuclear envelope, eventually filling the entire nucleus. The cell breaks up into smaller membrane bound fragments, which may contain individual organelles and remnants of the nucleus. These cellular fragments are rapidly phagocytosed by surrounding cells and as a result, apoptosis is not associated with an inflammatory response typical of other forms of cell death such as necrosis. On the other hand, in some tissues, cell death is associated with features that are characteristic of both apoptosis and necrosis. In these cases, the rate of apoptosis may greatly exceed the rate of phagocytosis such that the debris of apoptotic cells accumulates and breaks down by a process called secondary necrosis.

The mechanism by which apoptotic cell death occurs during normal development is thought to be related to competition among neurons for limited access to target-derived trophic factors. Induction of apoptosis by cytokine deprivation is a well-recognized phenomenon that frequently interferes with establishment of many cell types in culture. At least some trophic factors appear to enhance survival by inhibiting an endogenous apoptotic ("cell suicide") program. Cytokine withdrawal may either result in the activation of a cell death process or eliminate suppression of a default suicide program. [Fraser, et al., *Neurobiology* 6:71–80 (1996)].

Evidence indicates that the spread of damage in ischemia-related injury is due, at least in part, to release of transmitter(s) from damaged cells, triggering a massive calcium influx into adjacent cells, with consequent spread of cellular injury and release of neurotransmitters from injured cells.

Apoptosis is a common feature of the nervous system, occurring physiologically during development and pathologically in several diseases. Recent advances implicate several signaling pathways in the induction of apoptosis, after withdrawal of nerve growth factor. (Fraser, et al., 1996) Apoptosis can have particularly devastating consequences when it occurs pathologically in cells that do not normally regenerate, such as neurons. Because such cells are not replaced when they die, their loss can lead to debilitating and sometimes fatal dysfunction of the affected organ.

Numerous molecules have been identified as potential targets for regulation of apoptosis including, but not limited to "death receptors", e.g., CD95 (APO-1, FAS), TNF-R1, DR3, DR4/TRAIL-R1/APO-2, etc; adaptors, e.g., FADD/ MORT1, TRADD, MADD, RAIDD/CRADD, RIP, etc; caspases; apoptosis inhibitors, including, but not limited to Bcl-1, Bcl-$x_L$, A1, Mcl-1 and Bcl-w; and apoptosis promoters, including, but not limited to Bax, Bik/Nbk, Bak, Bad, and Bid [See Peter, et al., *Proc. Nat. Acad. Sci.* 94:12736–12737 (1997); Marte, et al. *Trends Biochem. Sci.* 9:355–358 (1997)].

Apoptosis has been implicated as the primary mode of cell death in models of increased intraocular pressure (IOP) in rats and other experimental procedures that cause retinal ganglion cell loss including optic nerve transection in monkeys, rabbits, and rats. Studies on the mechanism of retinal ganglion cell death in experimental glaucoma indicate that the cells die by apoptosis [Nickells, *J. Glaucoma* 5(5):345–356 (1996); Garcia-Valenzuela, et al., 1995; Laquis, et al., *Brain Res.* 784:100–104 (1998)].

B. NMDA Receptors and Ischemia

Cell death such as occurs in a variety of neurological diseases (e.g. stroke and epilepsy) may also be mediated by high levels of excitatory neurotransmitters [Lipton, et al., *N. Eng. J. Med.* 330:613–622 (1994)]. The primary excitatory neurotransmitter ("excitotoxin") in the brain is glutamate. Glutamate toxicity begins with the release of high levels of glutamate in response to various stimuli such as ischemia, because the high local concentration of glutamate over-stimulates cell surface receptors, e.g. the N-methyl-D-aspartate (NMDA) receptor.

Excitotoxicity has been implicated as a mechanism of neuronal death in acute and chronic neurologic diseases. Cerebral ischemia, head and spinal cord injury, and prolonged seizure activity are associated with excessive release of glutamate into the extracellular space and subsequent neurotoxicity. Accumulating evidence suggests that impairment of intracellular energy metabolism increases neuronal vulnerability to glutamate which, even when present at physiologic conditions, can damage neurons. Bittigau, et al., *J. Child Neurol.* 8:471–485 (1997). Accordingly, glutamate antagonists in combination with agents that selectively inhibit the multiple steps downstream of the excitotoxic cascade or help improve intracellular energy metabolism may slow the neurodegenerative process and offer a therapeutic approach to treat these disorders. (Bittigau, et al., 1997)

Free radicals may enhance the release of glutamate and thus enhance excitotoxicity [Pellegrini-Giamietro, et al., *J. Neurochem.* 51:1960–1963 (1988)]. NMDA receptor mediated neurotoxicity may depend, in part, on the generation of nitrous oxide and superoxide anion which react to form peroxynitrite and may contribute to a common pathway of injury that is relevant to numerous acute and chronic neurological disorder, including focal ischemia, Huntington's disease, Alzheimer's disease, amyotropic lateral sclerosis (ALS), AIDS dementia and other neurodegenerative diseases. [Bonfoco, et al., *Proc. Nat. Acad. Sci.* 92:7162–7166 (1995)]

The NMDA receptor complex contains an ion channel which gates $Na^+$, $K^+$ and $Ca^{2+}$ movement and is blocked in a dose dependent manner by $Mg^{2+}$. Membrane depolarization relieves this block and thereby allows activation of the complex through the action of glutamate (or NMDA) and glycine at their respective recognition sites. Various sites for modulation have been identified within the NMDA receptor complex, including, but not limited to, a glutamate recognition site, a glycine recognition site, a phencyclidine binding site and a polyamine modulatory zone. [Lehmann, et al., *Eur. J. Pharmacol.* 154:89–93 (1988)].

NMDA receptor antagonists, e.g. memantine, [Lagreze, et al., *Vis. Sci.* 39:1063–1066 (1998)], kynurenic acid [Toner and Stamford, *Eur. J. Pharmocol.* 340:133–143 (1997)], and 2-amino-7-phosphonoheptanoic acid, [Yamamoto and Tang,

*Toxicol. Lett.* 94:13–18 (1998)], have been shown to prevent NMDA receptor-mediated death of retinal ganglion cells in vivo. Numerous studies have demonstrated the neuroprotective effects of antagonists of postsynaptic N-methyl-D-aspartate (NMDA) and non-NMDA receptors in cerebral ischemia. Takizzawa, et al., *J. Cereb. Blood Flow Metab.* 4:611–618 (1995). Over-stimulation of the NMDA receptor opens $Ca^{2+}$ channels in the cell membrane, resulting in an overload of intracellular $Ca^{2+}$ and, in some neurons, activation of the enzyme nitric oxide synthase.

Toner and Stamford (1997) demonstrated that in vitro striatal dopamine release triggered by hypoxia/hypoglycemia is influenced by NMDA receptors and that drugs capable of interacting with NMDA receptors may modulate the effects of hypoxia/hypoglycemia and block NMDA-receptor mediated excitotoxicity.

C. Calcium Channels and Ischemia

Neuronal calcium channels generate both electrical and chemical signals when they open in response to membrane depolarization and allow calcium ions to flow down their electrochemical gradient. There exist a variety of types of calcium channels present in excitable cells, and many of these have been characterized based on gating properties, ionic conductance and pharmacology [e.g., Tsien et al., *TINS* (11)10:431–438 (1988)]. Calcium influx is believed to play a critical role in the cascade of biochemical events leading to neuronal cell death in a variety of pathological settings, including cerebral ischemia and myocardial infarction. Increases in intraneuronal $Ca^{2+}$ concentration, which accompany cerebral ischemia and brain injury, initiate a cascade of biochemical events that can eventually result in cell lysis and death. In certain experimental models of focal and global ischemia, certain calcium-channel blockers have been shown ameliorate neurologic damage. [Zornow, et al., *New Horizons* 1:107–114 (1996); U.S. Pat. No. 5,051,403]

L-type calcium channels are characterized as high threshold, dihydropyridine-sensitive channels that are found in almost all tissues. They have a voltage dependent activation, large single channel conductance, have a greater permeability to $Ba^{2+}$ than $Ca^{2+}$ and many are modulated by c-AMP dependent protein kinase. L-type calcium channel blockers are substances that are capable of blocking L-type calcium channels. Examples of L-type calcium channel blockers include certain dihydropyidines (such as nicardipine, nifedipine, isradipine, amlodipine, felodipine, and nimodipine), phenylalkylamines (verapamil), diltiazem (a benzothiazepine) and bepridil (a diaryaminopropylamine ether). L-type calcium channel blocking drugs have been approved in the United States for use in treating certain forms of angina, arrhythmias and hypertension.

N-type calcium channels are unique to neurons, and are characterized by single channel conductance, sensitivity to ω-conotoxin and insensitivity to dihydropyridine. [Bean, *Ann. Rev. Physiol.* 51:367–384 (1989)] The most potent and selective N-channel blocking compounds currently known are the "conopeptides," peptide toxins produced by pisciverous marine snails of the genus Conus. U.S. Pat. No. 5,051,403, incorporated herein by reference, describes how to make and use certain ω-conopeptides having defined binding/inhibitory properties, specifically, the synthetic ω-conotoxin peptide MVIIA (SNX-111) and derivatives thereof (e.g., SNX-194). U.S. Pat. No. 5,051,403 also teaches that these compounds provide neuroprotection against ischemic insult in gerbil and rat animal models of global and focal ischemia. SNX-111 is also known by the generic name "ziconotide."

D. Modulation of Apoptosis

Other compounds that may prevent apoptotic cell death include, e.g. nitric oxide synthase inhibitors which can protect neurons which have been exposed to activators of the NMDA receptor, aurintricarboxylic acid which prevents the activation of the nuclease that cleaves DNA, and antioxidant compounds such as 21-aminosteroids that act by potently blocking free radical lipid peroxidation. [Lipton and Rosenberg, *N. Eng. J. Med.* 330:613–622 (1994)]. It has also been suggested that cell damage in ischemia-reperfusion is due to enhanced activity of phospholipases and proteases, leading to release of free fatty acids and their breakdown products and to degradation of cytoskeletal proteins. It is equally clear that a coupling exists between influx of calcium into cells and their production of reactive oxygen species, such as $O_2$, $H_2O_2$, and OH. A coupling has been demonstrated among glutamate release, calcium influx, and enhanced production of reactive metabolites such as $O_2$, OH, and nitric oxide. The combination of $O_2$ and nitric oxide can yield peroxynitrate, a metabolite with potentially devastating effects to cells. Certain conditions, notably mitochondrial calcium accumulation and oxidative stress are known to trigger production of reactive oxygen species. [Kristian and Siesjo, *Stroke* 3:705–718 (1998)]

Candidate drugs for modulating apoptosis include drugs that; (1) antagonize or inhibit different stages of the apoptotic pathway, e.g., the various intracellular targets set forth above, (2) affect $Ca^{2+}$ flux, or (3) interfere with stimulation of NMDA receptors, etc. Such drugs can be screened in vitro according to the assay methods set forth herein.

E. Growth Factors and Glaucoma

In some cases, glaucoma is associated with damage to the optic nerve, which normally supplies growth factors to the various cells of the eye including the retinal ganglion cells. Damage to the optic nerve can result in a reduction or elimination of the supply of growth factors to the various cells of the eye. [Nickells, *J. Glaucoma* 5:345–356 (1996)].

Retinal ganglion cells, like most neurons, are dependent on growth factors for survival in vivo and in vitro. These factors are generally small peptides that are classified as either neurotrophins, neurotrophic factors, cytokines, or growth factors. They act by binding to cell surface receptors on target cells, which in turn stimulates a cascade of molecular events that affect multiple essential functions of cellular metabolism. Growth factors that are necessary for survival of retinal ganglion cells include neurotrophin brain-derived neurotrophic factor [BDNF, Cohen-Cory and Fraser, *Neuron* 12:747–61 (1994)], ciliary neurotrophic factor (CNTF), insulin-like growth factor-1 (IGF-1), insulin, and forskolin. [Meyer-Franke, et al., *Neuron* 15:805–189 (1995)] Neurotrophic factor deprivation may be a cause of apoptosis in retinal ganglion cells. In the adult retina, anything that disrupts the flow of BDNF (and/or other neurotrophins) from the brain to the retina hypothetically compromises the viability of retinal ganglion cells. This includes optic nerve transection, which is known to stimulate ganglion cell apoptosis. The injection of exogenous BDNF into the vitreous of rat eyes significantly delays the apoptosis of ganglion cells after optic nerve transection. Increased IOP (e.g. as is known to occur in glaucoma) has been demonstrated to cause an interruption of axoplasmic transport in human and experimental glaucoma. Accordingly, this blockage may prevent the flow of one or more growth factors to retinal ganglion cells and thereby stimulate apoptosis.

III. In Vitro Assays for Ischemic Cell Damage

In accordance with the present invention, substantially homogeneous excitable cells in primary culture provide a predictive in vitro assay for selecting compounds that are candidates for treating disease conditions associated with ischemic cell death, such as myocardial infarction, stroke, glaucoma, and other neurodegenerative diseases. Various neurodegenerative diseases which may involve apoptotic cell death, include, but are not limited to, Alzheimer's Disease (Kim, et al., *Science* 277:373–376 (1997)), ALS and motor neuron degeneration (Greenlund, et al., *Neuron* 14:303–315 (1995)), Parkinson's disease (Ghosh, et al., *Science* 263:1618–1623 (1994)), peripheral neuropathies, (Batistatou, et al., *J. Cell. Biol.* 122:523–532 (1993)), Down's Syndrome (Busciglio, et al., *Nature* 378:776–779 (1995)), age related macular degeneration (ARMD) (Hinton, et al., *Arch. Ophthalmol.* 116:203–209 (1998)), Huntington's Disease (Goldberg, et al., *Nat. Genetic* 13:442–449 (1996)), spinal muscular atrophy (Liston, et al., *Nature* 379:349–353 (1996)), and HIV encephalitis (Lazdins, et al. *J. Exp. Med.* 185:81–90 (1997)).

This section describes exemplary assays using primary cultures of excitable cells that can be used in the assays of the invention.

A. Retinal Ganglion Cell Assay

According to one embodiment of the invention, substantially homogeneous primary cultures of retinal ganglion cells (RGCs) may be employed in the assay. These are central nervous system neurons that extend their axons from the retina through the optic nerve either to the geniculate nucleus or (as in the rat) directly to the superior colliculus or optic tectum. RGCs relay visual signals from the retina to the rest of the brain. These glutamatergic neurons can be purified to greater than 99% purity from either the rat or mouse retina using monoclonal antibodies against the surface protein Thy 1 by an immunopanning method detailed in Example 1, below. RGCs can be kept in primary culture for a period of four weeks or longer.

According to the present invention, RCGs are particularly useful as a general in vitro model for ischemia, such as that associated with stroke, for a specialized form of ischemia such as that which manifests in glaucoma and for neurodegenerative diseases in general. The methods of the present invention are based on an evaluation of apoptotic cell death and include an in vitro model for ischemia, wherein cell death is induced by oxygen/glucose deprivation, a model for optic nerve ischemia (i.e. glaucoma), and for cerebral ischemia, wherein cell death is induced by growth factor deprivation or oxygen/glucose deprivation together with growth factor deprivation.

1. Purification and Primary Culture of Retinal Ganglion Cells

RGCs from postnatal day 8 (P8) Sprague-Dawley rats can be purified according to methods known in the art (Barres, et al, *Neuron* 1:791–803, 1988; Meyer-Franke, et al, *Neuron* 15:805–819, 1995) and as described in Examples 1A–1C, below. This procedure results in a population of RCGs that is at least 80% and generally greater than 99% homogeneous (free from other cell types), as assessed by immunostaining (Barres, et al, *Neuron* 1:791–803, 1988). Purified retinal ganglion cells are plated onto tissue culture plastic precoated with poly-D-lysine and merosin, and cultured in serum-free Neurobasal medium (Gibco, Ground Island, N.Y.) containing various supplements, as described in Example 1D.

2. Method of Screening Retinal Ganglion Cells

This section describes in vitro assays which are useful for evaluating the extent of RGC death in the evaluation of one or more test compounds. Generally, as discussed in Section IV herein, cells are subjected to ischemic and/or growth factor/glucose challenge. Test compound is added before, during or after such challenge, and cell survival is assessed at a selected time thereafter. Cell death may be detected by staining of cells with propidium iodide, by use of mitochondrial dyes (e.g. MTT) to detect necrosis, or by use of assays specific to apoptotic cell death, e.g. staining with annexin V [Vermes, et al., *J. Immunol. Meth.* 184:39–51 (1995); Walton, et al., *Neuroreport* 8(18):3871–3875 (1997)]. Necrotic cell death may be distinguished from apoptotic cell death by using a combination of the assays for cell viability, which are described below.

a. Assay for Necrotic Cell Death

Necrosis is a passive process in which collapse of internal homeostasis leads to cellular dissolution (Wyllie, et al., 1980a). The process involves loss of integrity of the plasma membrane and subsequent swelling, followed by lysis of the cell (Schwartz, et al., 1993). Propidium iodide (PI) is known by those in the art to bind to the DNA of cells undergoing primary and secondary necrosis [Vitale, et al., *Histochemistry* 100:223–229 (1993)]. Necrotic cell death is characterized by loss of cell membrane integrity and permeability to dyes such as PI. Necrosis may be distinguished from apoptosis in that cell membranes remain intact in the early stages of apoptosis. As a consequence a dye exclusion assay using PI must be used in parallel with an assay for apoptosis, as described below in order to distinguish apoptotic from necrotic cell death, and the percentage of cells undergoing necrosis may be measured at various times after oxygen/glucose or growth factor deprivation. Cells in later stages of apoptosis (i.e. cells undergoing secondary necrosis) may also exhibit a loss of cell membrane integrity and stain positive with PI. [Vitale, et al., (1993)].

b. Assay for Apoptotic Cell Death

Detection of programmed cell death or apoptosis may be accomplished as will be appreciated by those in the art. The percentage of cells undergoing apoptosis may be measured at various times after oxygen/glucose or growth factor deprivation. The morphology of cells undergoing apoptotic cell death is characterized by a shrinking of the cell cytoplasm and nucleus and condensation and fragmentation of the chromatin (Wyllie, et al., *J. Pathol.* 142:67–77, 1984) One of the earliest events in programmed cell death is the translocation of phosphatidylserine, a membrane phospholipid from the inner side of the plasma membrane to the outer side. Annexin V is a calcium-dependent phospholipid binding protein that has a high affinity for membrane bound phosphatidylserine and thus annexin V-FITC can be used to stain cells undergoing apoptosis with detection and quantitation of apoptotic cells by flow cytometry or any other method of fluorescent detection. [Vermes, et al., (1995); Walton, et al., (1997)] Accordingly, annexin V can be used as an affinity ligand in solution, attached to a solid support such as a bead, a surface etc., binding apoptotic cells. Similarly, annexin V is the basis for a fluorescent-activated cell sorting (FACS) separation process and assay method.

c. Quantitation of Cell Survival

Cell survival may be measured at various times after oxygen/glucose or growth factor deprivation using the MTT assay. The MTT assay is a measure of mitochondrial activity in cells and is a general indicator of cell viability, based on the ability of living cells to take in and process the dye known as MTT (3-(4,5-dimethylthiazol-2-yl)-2,5-diphenyl tetrazolium bromide; Sigma Chemical Co., St. Louis, Mo.), an active process which dead cells cannot complete. The assay was performed as previously described [Mosmann, et al., *J. Immunol. Meth.* 65:55–63, 1983; Barres, et al., *Cell* 70:31–46, 1992; Barres, et al., *Development* 118:283–295, 1993a]. MTT was added to culture and incubated at 37 C. for 1 hr. Viable cells with active mitochondria cleave the tetrazolium ring into a visible dark blue formazan reaction product. Viable and dead cells are counted by bright field microscopy at various times, e.g. 24, 48, or 72 hours after oxygen/glucose and/or growth factor deprivation. All values are reported as the mean (average) the standard error of the mean (SEM) for at least three replicate cultures.

d. Interpretation of Results

Cell death can be evaluated using light microscopy following the staining of cells with the mitochondrial dye MTT, or by fluorescent/light microscopy following the staining of cells with propidium iodide (PI) or Annexin V. Cell death was also evaluated by FACS analysis following staining with PI or aimexin V. The percentage of apoptotic cells may be determined based on the percentage of annexin V positive cells that are not PI or MTT positive. However, there are some cells in later stages of apoptosis that also exhibit a loss of cell membrane integrity and stain positive with PI (i.e. they are undergoing secondary necrosis).

B. Myocyte Assay

Primary myocyte cultures can be prepared from hearts removed from neonatal rats, according to methods known in the art and described in Example 5 herein. Primary cultures prepared according to these methods result in cell populations that are at least about 80% homogeneous, and therefore are substantially homogeneous, in accord with the present invention.

Assays are set up similar to the methods described with respect to RCGs, above. Generally, cells are used 5–6 days after initial plating. Ischemia is induced in a humidified 37° C. incubator within an air-tight hypoxia chamber maintained with <0.1% oxygen/1% carbon dioxide and the balance nitrogen, with cells in a glucose-free medium. Further procedures and methods of assessment are as described above.

Figure 11:
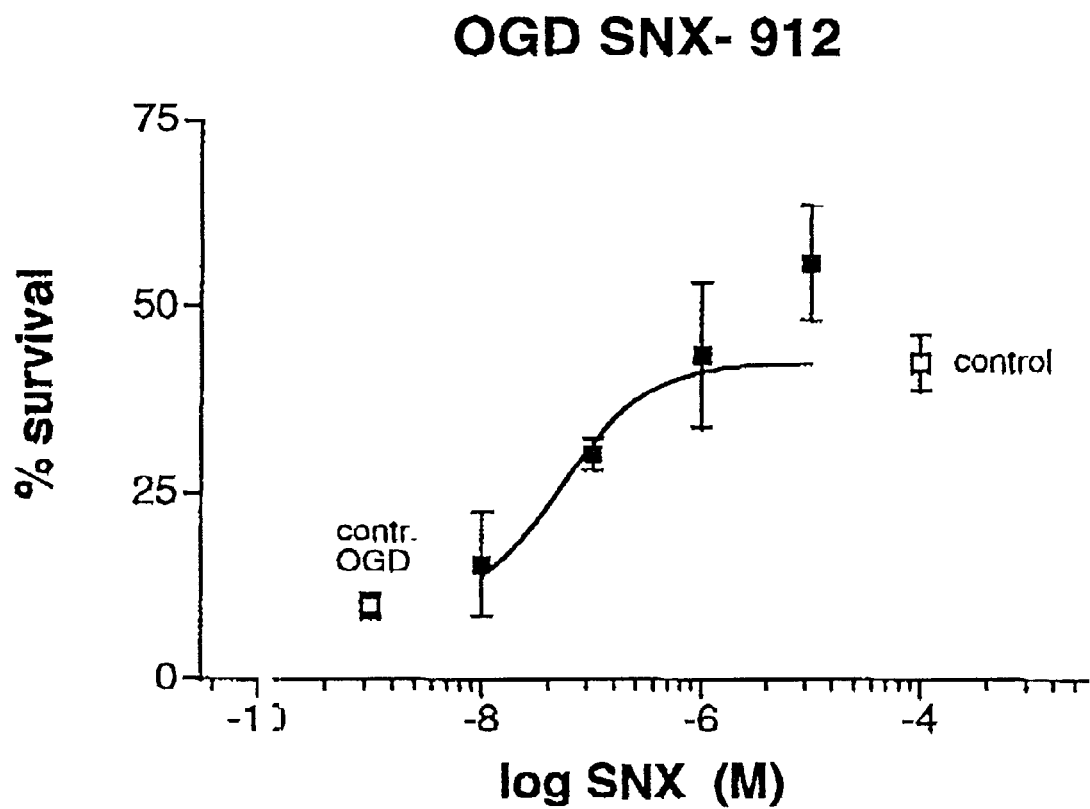
FIG. 11 shows the effect of varying concentrations of SNX-912 on survival of myocytes subjected to hypoxia/glucose deprivation, where OGD indicates percent survival of cells in the absence of added compound, and "contr." represents cells that were not subjected to hypoxia/glucose deprivation.

In studies carried out in support of the present invention, a compound referred to as SNX-912 was tested for its cell protective activity in this assay, as detailed in Example 5. FIG. 11 shows that this compound was protective against the ischemic insult against the myocytes, in a dose-dependent manner. SNX-912, and related protective bis-benzimidazole compounds are described in pending U.S. provisional applications No. 60/137,618, filed Jun. 4, 1999 and No. 60/138, 855, filed Jun. 11, 1999, both of which are hereby incorporated herein by reference.

IV. Method of Screening Candidate Compounds

A. In vitro Models of Ischemia

This section describes in vitro assays useful for identifying candidate compounds that are effective to treat ischemia-related cellular damage. The methods of the present invention have been used to evaluate test compounds for their relative efficacy in improving or reducing the percentage of excitable cells, exemplified by RGCs and myocytes, that die in vitro following oxygen/glucose-induced ischemia.

1. Oxygen/Glucose Deprivation (OGD) in Retinal Ganglion Cells

Retinal ganglion cells were isolated as described above and in Example 1.

Retinal ganglion cells are grown in 96-well plates for 5 days in serum-free medium. The cells are maintained in medium containing glucose in a balanced salt solution (EBSS, Gibco), containing glucose for control cells, and lacking glucose for test cells (oxygen/glucose-deprived cells). Control cells are further incubated in a 5% $CO_2$ incubator while test cells are deprived of oxygen in an anaerobic chamber for about 3 hours. After about 3 hours, control and test cells are washed three times with a glucose-containing medium and cultured for approximately 24 to 48 additional hours in a 5% $CO_2$ incubator. Cell viability is evaluated by MTT assay and by staining cells with FITC-coupled annexin V (ApoAlert Kit, Clonetech) and PI at 24 and 48 hours after OGD, followed by microscopy. Preferably, OGD is sufficient to produce cell death in at least 25% of RGCs subjected to the challenge. More preferably, OGD is sufficient to produce cell death in at least 35 or 40% of RGCs subjected to the challenge, and most preferably, OGD is sufficient to produce cell death in at least 50 to 75% of RGCs subjected to the challenge.

Figure 3:
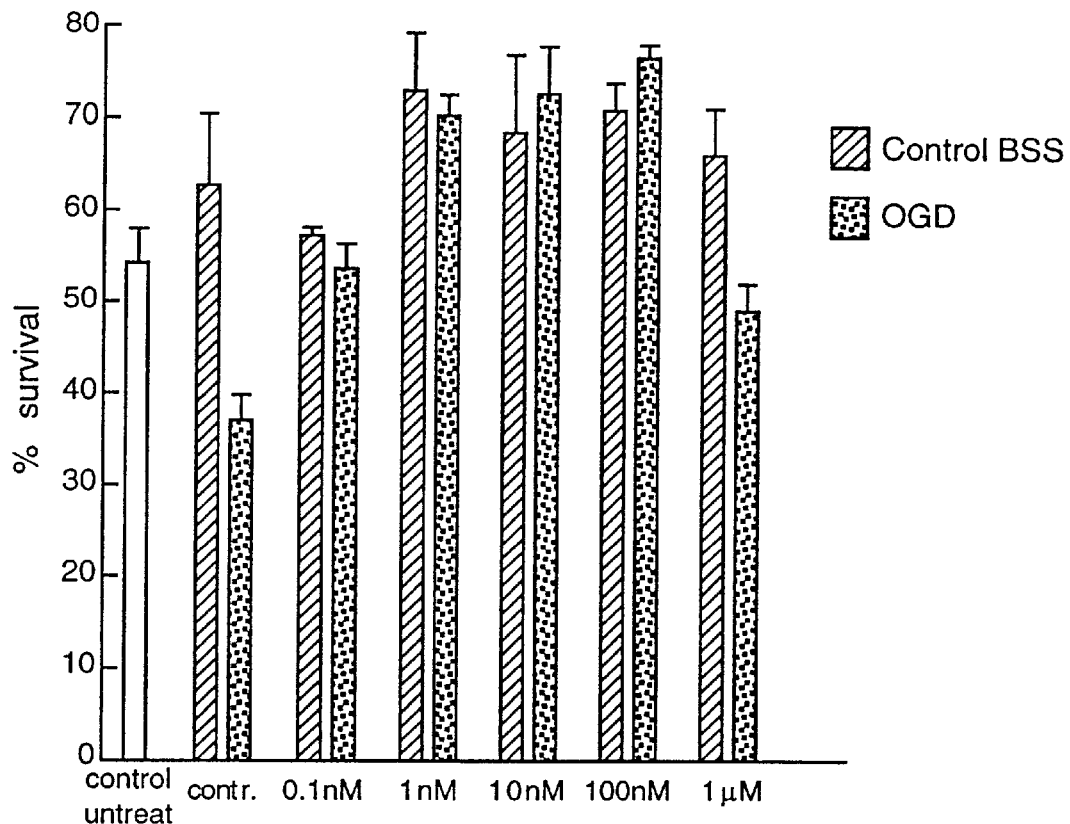
FIG. 3 shows the effect of pre-treatment of retinal ganglion cells with various concentrations of SNX-194 beginning 30 minutes prior to OGD and continuing for up to 48 hours after OGD, as indicated by the percentage survival of retinal ganglion cells at 48 hours after oxygen/glucose deprivation (OGD). Also included is a BSS control (absent OGD).
Figure 4:
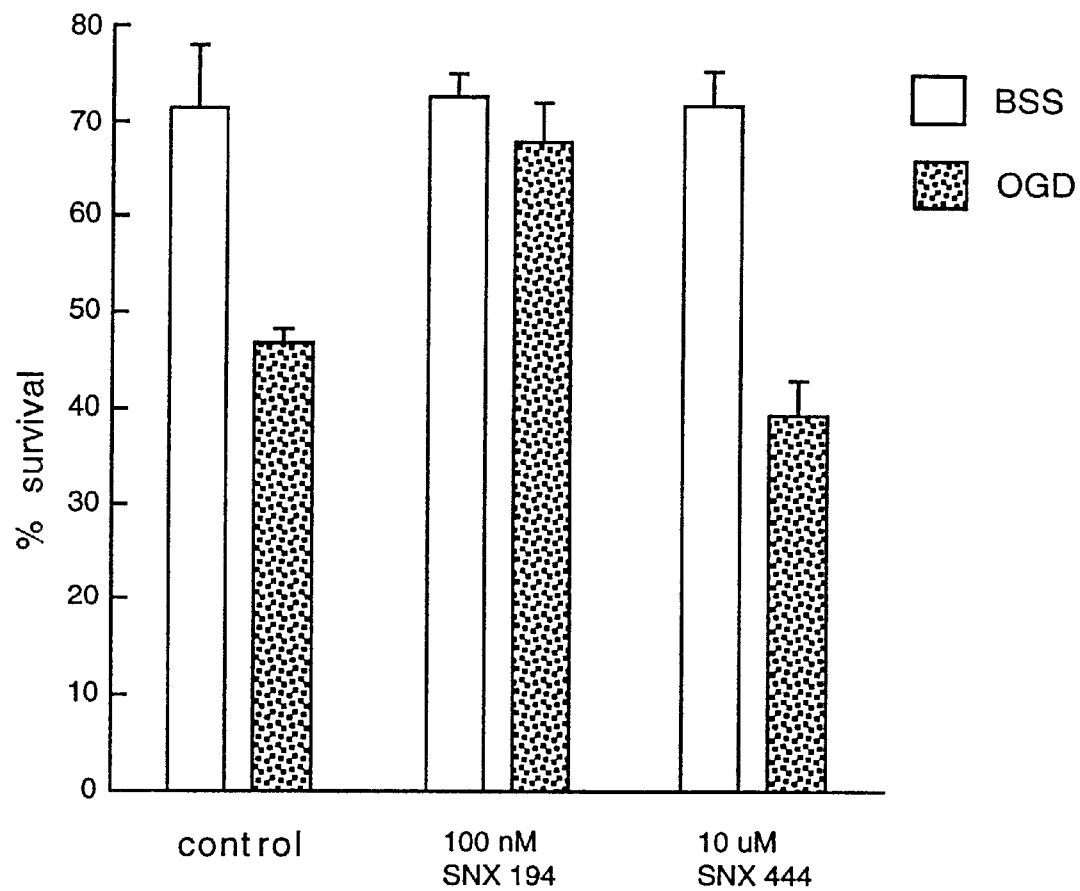
FIG. 4 shows a comparison of the effect of pre-treatment of retinal ganglion cells with a 10 µM solution of negative control peptide SNX-444 versus a 100 nM solution of the SNX-194 beginning 30 minutes prior to OGD, and continuing for up to 48 hours after OGD, as indicated by the percentage survival of retinal ganglion cells at 48 hours after oxygen/glucose deprivation (OGD). Also included is a BSS control (absent OGD).
Figure 5:
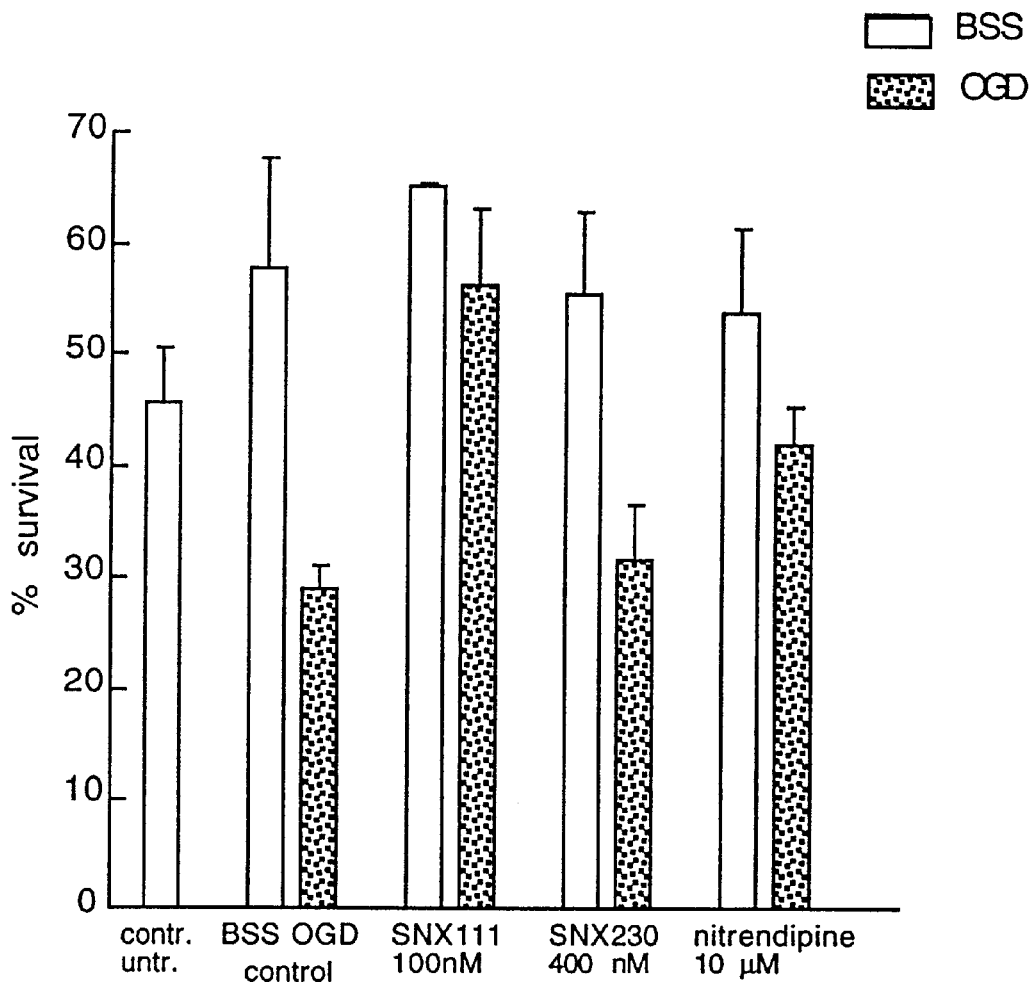
FIG. 5 shows the effect of pre-treatment of retinal ganglion cells with a 100 nM solution of SNX-111, a 400 nM solution of SNX-230, and a 10 µM solution of nitrendipine, beginning 30 minutes prior to OGD and continuing for up to 48 hours after OGD, as indicated by the percentage survival of retinal ganglion cells at 48 hours after oxygen/glucose deprivation (OGD). Also included are a BSS control (absent OGD) and an OGD control (absent treatment).

In studies carried out in support of the present invention, the conopeptide, SNX-194 has demonstrated biological activity in protecting oxygen/glucose-deprived RGCs from apoptotic cell death in the in vitro RGC assay for ischemia as described in Example 2C (see FIGS. 3 and 4). SNX-111 also demonstrated such protective activity, while SNX-230 was devoid of such activity (FIG. 5). SNX-111 (also known as MVIIA) and SNX-194 are N-type calcium channel compounds described in U.S. Pat. No. 5,051,403, incorporated herein by reference.

The NMDA receptor antagonists, flufenamic acid, DL-2-amino-5-phosphonovaleric acid (AP-5), and DL-2-amino-7-phosphonovaleric acid (AP-7), and to a lesser extent mefenamic acid and meclofenamic acid, have demonstrated biological activity in protecting oxygen/glucose-deprived RGCs from apoptotic cell death in the in vitro RGC assay for ischemia as described in Example 2D.

2. OGD in Cortical Cells

In vitro rat cortical cell cultures are prepared from cerebral hemispheres of fetal rat at day 17 of gestation by dissociation with 0.2% trypsin, and cultured in vessels treated with poly-L-lysine for 4 days. Non-neuronal cell division is halted by 1 day exposure to 40 $\mu$m Ara-C. Cytotoxicity is estimated by the measurement of lactate dehydrogenase (LDH) release into the extracellular fluid of damaged cells after 24 hours using a spectrophotometric method in conjunction with an assessment of neuronal cell injury by phase-contrast microscopy. Extracellular LDH and neuronal disintegration is increased by exposure of cortical neuronal cells to potassium cyanide and NMDA for about 24 hours. This effect is partially prevented by co-exposure to 1.0 mM DL-2-amino-7-phosphonovaleric acid (AP-7), a selective NMDA receptor antagonist, 1.0 mM melatonin, a potent hydroxyl and peroxyl radical scavenger and 1.0 mM $N^G$-nitro-L-arginine, an inhibitor of NO synthase. [Yamarnoto and Tang, *Toxicol. Lett.* 94:13–18 (1998)] See also, Evans, et al., *Br. J. Pharmacol.* 75(1):65–75 (1982), and Kral, et al., *Brain Res.* 612:278–288 (1993) for the protective effect of DL-2-amino-5-phosphonovaleric acid (AP-5) in an in vitro model for cerebral ischemia in rat neocortical tissue slices. A structurally-related NMDA receptor antagonist, memantine, has been shown to prevent NMDA receptor-mediated death of retinal ganglion cells in an in vivo rat model for ischemia induced by elevating the intraocular pressure. Approximately a 30% and 20% increase in the number of surviving retinal ganglion cells was observed when memantine was administered before or within 30 minutes of retinal ischemia, respectively. (Lagreze, et al., 1998).

3. Growth-factor Deprived Retinal Ganglion Cells

The invention also includes a method for evaluating the relative efficacy of test compounds based on decreased apoptosis-related cell death in growth factor-deprived (GFD) retinal ganglion cells in vitro. This assay is particularly useful in the discovery of candidate compounds for treating glaucoma. Glaucoma is a condition that is associated with increased intraocular pressure, which results in decreased blood flow and an ischemic-like condition. In some cases, glaucoma is also associated with damage to the optic nerve, which normally supplies growth factors to the various cells of the eye including the retinal ganglion cells. (Nickells, *J. Glaucoma* 5:345–356 (1996). Studies on retinal ganglion cell death in experimental glaucoma indicate that most if not all the retinal cell death is apoptotic in nature (Nickells, *J. Glaucoma* 5(5):345–356 (1996); Garcia-Valenzuela, et al., *Exp. Eye Res.* 61(1):33–44 (1995); Laquis, et al., *Brain Res.* 784:100–104 (1998).

In studies carried out in support of the present invention, it has been demonstrated that when RGCs are cultured in Neurobasal medium lacking growth factors including insulin, BDNF, CNTF and forskolin, the cells die via apoptosis (Meyer-Franke, 1995), and that such an assay is predictive of efficacy in glaucoma. Briefly, for this assay, retinal ganglion cells are washed three times in Neurobasal medium (0.02% BSA) for 45 minutes each time, and cultured in 96-well plates for about 5 days in serum-free medium, containing Sato-Bottenstein and B27 supplements. The medium also contains growth factors including insulin, BDNF, CNTF and forskolin in a balanced salt solution (EBSS, Gibco), for control cells, and lacks growth factors for test cells [growth factor-deprived (GFD) cells]. All cells are further incubated in a 5% $CO_2$ incubator for about 3 hours, after which control and test cells are washed and cultured for about 48 additional hours in a 5% $CO_2$ incubator. Test compounds are added to the RGC culture for about 48 hours after growth factors have been washed out. One or more test compounds may be evaluated in parallel in both the OGD and GFD retinal ganglion cell assays. Test compounds may protect cells from cell death induced in RGCs by one or both of OGD and GFD and the effective concentrations may or may not be the same.

Preferably, GFD is sufficient to produce cell death in at least 25% of RGCs subjected to the challenge. More preferably, OGD or GED is sufficient to produce cell death in at least 35 or 40% of RGCs subjected to the challenge, and most preferably, OGD or GFD is sufficient to produce cell death in at least 50% of RGCs subjected to the challenge. The test compounds determined to be efficacious in reducing cell death in in vitro growth factor-deprived RGCs by at least 50%, preferably 75% and more preferably 85–100%, relative to untreated control RGCs, are further tested in established animal models for ischemia.

B. In vivo Models of Ischemia

Candidate compounds selected by the methods described above can be validated in in vivo models of ischemia. This section describes exemplary models for this purpose. Persons skilled in the art will appreciate that other models can be substituted for the models described below.

1. Cerebral Ischemia

Various in vivo models have been described that produce neuronal ischemia in the central nervous system. Exemplary models include gerbil 2-vessel occlusion model of global ischemia produced by transient occlusion of carotid arteries [Kirino, *Brain Res.* 239:57–69 (1982)], the rat four-vessel occlusion model of global ischemia [Pulsinelli, et al., *Stroke* 10:267–272 (1979)], and the rat middle cerebral artery occlusion (MCAO) model of focal ischemia [Tamura, et al., *J. Cereb. Blood Flow Metab.* 1:53 (1981)].

The test compounds determined to be efficacious in reducing cell death in in vitro oxygen/glucose-deprived RGCs by at least 25%, preferably 40% and more preferably 75%, relative to untreated control RGCs, are further tested in established animal models for ischemia. By way of example, SNX-111, was shown to be biologically active in the gerbil model for global ischemia (see Example 3A below), while SNX-230, which was ineffective in an RCG assay of the invention, was not neuroprotective in such in vivo models.

a. Gerbil Model of Global Ischemia

Mongolian gerbils have been used as a model for cerebral ischemia and infarction. [Kirino, *Brain Res.* 239:57–69 (1982)]. The gerbil lacks an interconnection between the carotid and vertebro-basilar circulation such that one can easily produce cerebral ischemia by occlusion of the common carotid arteries of the neck. The gerbil brain subjected to transient bilateral carotid occlusion for no longer than 5 minutes can produce a typical ischemic lesion in the CA1 region of the hippocampus. For clinical comparisons, the ischemia produced in this model has been likened to that produced by cardiac arrest, since all blood flow to the brain is stopped for a fixed period, typically 5–10 minutes.

Although some differences in particular sequelae have been noted between species, gerbils exhibit the same kind of selective regional damage resulting from ischemia as is found in other mammals, including humans. In particular, the characteristic secondary damage observed in the hippocampal CA1 region is similar to that seen in other mammals, including humans. Neurons in this area, and especially pyramidal neurons, exhibit a delayed neuronal death over a period of up to 4 days after ischemic injury.

b. Rat Four-Vessel Occlusion Model of Global Ischemia

The rat model encompasses a procedure for producing temporary occlusion and produces an ischemia that mimics conditions in the human brain following cardiac arrest, including a temporary ischemic event, typically 5–30 minutes, which occurs in an unanesthetized state. In most rats, the ischemic event is not accompanied by generalized seizures, and animals that have seizures can be excluded from the study. The occlusion procedure allows the animals to be easily monitored, maintained and analyzed. [Pulsinelli, et al., (1979)].

The selective N-type calcium channel blocker, SNX-111, has been demonstrated to be neuroprotective in both the rat 4 vessel occlusion model of ischemia and a model of transient middle cerebral artery occlusion focal ischemia. [Buchan, et al., *J. Cereb. Blood Flow Metab.* 14(6):903–910 (1994)].

SNX-111 provided neuroprotection when a single bolus injection was administered intravenously up to 24 hr after the ischemic insult. [Valentino, et al., *Proc. Natl. Acad. Sci.* 16:7894–7897 (1990)]. SNX-111 significantly reduced total amount of extracellular glutamate during the experiment and the peak value of glutamate after occlusion. These results suggest that SNX-111 has a protective effect against focal ischemia and may impact glutamate release, although SNX-111 may also affect the release of other neurotransmitters. (Valentino, et al., (1990)

In contrast to SNX-111, SNX-230 failed to show any efficacy in the four-vessel occlusion model of ischemia. However, mnicrodialysis studies indicated that SNX-111 was 3 orders of magnitude less potent in blocking potassium-induced glutamate release in the hippocampus than the conopeptide SNX-230, indicating that the ability of a conopeptide to block excitatory amino acid release does not necessarily correlate with its neuroprotective efficacy. [Valentino, et al., *Proc. Natl. Acad. Sci.* 16:7894–7897 (1990)].

c. MCAO Filament Model of Focal Ischemia

Animal stroke models with focal cerebral infarction, which have been established in cat, dog, primates, gerbils and rats are believed to be directly relevant to clinical experience. A commonly used focal ischemia model in the rat is the right middle cerebral artery occlusion (MCAO) model developed by Tamura and co-workers. [Hsu, et al., *Cerebral Ischemia and Resuscitation* 3:47–59 (1990)]. Briefly, Male Wistar rats weighing 310–340 g are anaesthetized with 3–3.5% halothane, and orally intubated. Nylon monofilament fishing thread or silicone rubber-coated nylon fishing line, with an outer diameter of approximately 28 mm is used to occlude the middle cerebral artery, by insertion from the external carotid artery, as described in Hsu, et al., 1990. The MCAO model requires no craniectomy and allows easy reperfusion, however, temperature can influence focal ischemic damage due to middle cerebral artery (MCA) occlusion, but this complication can be avoided by anesthesia and/or cooling of awake animals. [Zhao, et al., *Brain Research* 649:253–259 (1994)]

d. Other Confirmatory Models

One common consequence of cerebral ischemia in animals is hyperactivity, which can be seen as pacing behavior within a few hours of occlusion, and can be observed up to several days later. Briefly, gerbils are tested individually for 60 minutes, at 1 and 3 days after occlusion, with cumulative activity counts recorded every 15 minutes for statistical analysis by comparison to baseline activity measured before surgery. Results may be quantitated, e.g. with an Automex activity monitor (Columbia Instruments, Columbus, Ohio), which record perturbations of a radiofrequency field. Occlusion alone has been demonstrated to produce a significant rise in activity level, beginning one day after occlusion, and continuing over a three-day period, indicating permanent behavioral damage. Occluded animals treated with SNX-111 showed lower-than baseline values at one day, and at three days, treated animals showed near-normal levels of activity, indicating that the SNX-111 treatment provided protection against ischemia-induced hyperactivity. (U.S. Pat. No. 5,051,403). Damage to the hippocampal region of the brain is also known to produce deficits in spatial learning and memory, and therefore ischemic damage to hippocampal cells, might also be accompanied by loss of functional activity related to short-term memory. A test which has been widely applied as a measure of short-term memory in experimental animals is one in which animals are placed in the base of the stem of a Y maze, and allowed to enter either of the two Y arms. When the animal enters an arm, a door is shut behind it. After 5 seconds, the animal is returned to its home cage for 2 to 12 minutes, then the animal is run in the maze again in the same way. Most normal animals will enter the arm that was not entered on the first trial. In a test procedure, 3 days after induction of ischemia, the ischemia-associated loss of short term memory that was evident in gerbils that received simultaneous intracerebroventricular (IC) administration of vehicle was completely prevented by IC administration of 0.1 or 0.3 g. SNX-111. (See U.S. Pat. No. 5,051,403).

In a rat model of traumatic brain injury, cellular calcium homeostasis is perturbed, with an overload of cytosolic calcium and excessive calcium absorbed on the mitochondrial membrane, resulting in impairment of the mitochondrial respiratory chain-linked oxidative phosphorylation. SNX-111 has been shown to modulate the impact on mitochondrial dysfunction in this model [Verweij, *Neurol. Res.* 3:334–339 (Jun. 19, 1997)]. In addition, SNX-111 has also been shown to significantly attenuate overall cortical ischemic neuronal damage in a rabbit model of focal cerebral ischemia. [Perez and Pinzon, *Journal of Neurol Science* 153(1):25–31 (1997)]

In summary, the foregoing description shows that a test compound that shows efficacy in protecting cells against ischemic insult in assays of the present invention are also shown to be neuroprotective in in vivo models.

2. In vivo Models of Glaucoma

Various in vivo models have been described that mimic the mechanism of cell death believed to occur in glaucoma, most notably, various rat models such as the model based on increased intraocular pressure (IOP) as described e.g. by Garcia-Valenzaela, et al., 1995; Lagreze et al., 1998; Morrison, et al., *Exp Eye Res.* 64:85–96 (1997) and Berkelaar, et al., 1994 and the models based on optic nerve crush lesion as described by Villegas-Perez, et al., 1993, Isenmann et al, 1997, and others. This section describes exemplary assays used to verify the efficacy of candidate compounds in accordance with the present invention.

a. Intraocular Pressure Model

Experimental glaucoma may be induced in the rat by blocking the venous return from the anterior chamber of the eye. Changes in retinal ganglion cells can be studied at various time intervals after elevation of intraocular pressure (IOP). Retinas can then be analyzed for signs of apoptosis. (Garcia-Valenzuela, et al., 1995) In summary, adult Wistar rats (275–325 g) were anesthetized and their heads were mounted on a stereotaxic apparatus. Fast Blue dye was injected into different sites across each superior colliculus and five days after the injection increased IOP was surgically induced by applying an ophthalmic cautery to two large veins per eye and completely blocking the venous return through each vessel. The IOP measurements were taken with a Mentor I pneumatonometer (BioRad, Richmond, Calif.) with IOP raised to an average of 63.3 mm Hg for four vein-occluded eyes and continuous occurrence of cell death was observed starting a few days after cauterization. (Garcia-Valenzuela, et al., 1995)

b. Optic Nerve Degeneration

The rat optic nerve represents a widely used model to study degenerate and regenerative processes in the central nervous system (CNS). [Bahr, *Exp. Neurol.* 111:65–73 (1991); Bahr and Bonhoeffer, *Trends Neurosci.* 17:473–479 (1994); Berkelaar, et al., *J. Neurosci.* 14:4368–4374 (1994); Schaden, et al., *J. Neurobiol.* 25:1570–1578 (1994)]. Axotomy and crush lesion of the optic nerve in adult rats have been shown to result in the death of many retinal ganglion cells within a few weeks [Villegas-Perez, et al., *Neurobiol.* 24:23–36 (1993)].

Isenmann, et al., *Eur. J. Neurosci.* 9:1763–1772 (1997), demonstrated that cell death following intraorbital optic nerve crush occurred by an apoptotic mechanism by examining changes in the level of expression of the apoptosis-associated proteins relative to RGC death. In these studies, adult female Sprague-Dawley (S/D) rats (240–280 grams) were anaesthetized, the left eye bulb carefully mobilized and the optic nerve crushed with care not to injure the eye or impair the blood supply. Rats were examined at various times after the operation. Retinae were examined histologically after rats were killed by an overdose of anaesthetic, both eyes removed, immediately snap-frozen and stored at −80 C. until sectioning with the right eye serving as a control for each animal.

Cryostat sections of retinae were stained with haematoxylin and eosin and, on separate sections with cresyl violet for morphological analysis of the retina and RGCs. Nuclear morphology was also evaluated under epiflourescence in sections stained with 4,6-diaminido-2-phenylindole (DAPI), and fluorescence microscopy was used to evaluate cell body and nuclear morphology of RGCs. In addition, the authors used terminal transferase-mediated dUTP nick-end-labeling (TUNEL) to detect DNA strand breaks in retinal sections.

Nuclei of most TUNEL-labeled cells exhibited histological characteristics of apoptotic cells, including nuclear shrinkage, margination, homogenization or condensation of the chromatin and in some cases, nuclear fragmentation. The results of TUNEL staining and analysis of nuclear morphology provided biochemical and histological evidence that degeneration of RGCs occurs mainly between 2 days and 2 weeks after proximal optic nerve crush and that degeneration occurs by an apoptotic mechanism. (Isenmann, et al., 1997)

The neuroprotective effect of NMDA receptor antagonists has been evaluated in approximately 300 gram Sprague/Dawley rats in a retinal ischemia model of IOP. After a short inhalation of isoflourane, IOP was artificially increased by injecting rats with 4 ml of 2% 2,2,2-tribromo methanol in 2-methyl-2-butanol (1 gm/ml) diluted with saline, IP, tetracaine hydrochloride was put into both eyes, the head fixed in a stereotactic frame, and a 0.3 mm steel cannula inserted through the peripheral cornea into the anterior chamber of the left eye with the intraocular pressure elevated to 120 mm Hg. After 1 hour, the pressure was lowered, the cannula removed and gentamycin ointment applied.

Various treatment regimes were delivered to Sprague-Dawley rats including (1) 20 mg/kg/day memantine (an NMDA receptor antagonist), delivered by an osmotic pump (Alzet, Palo Alto, Calif.) implanted subcutaneously in the backs of animals starting 2 days before induction of ischemia, with a 20 mg/kg bolus of memantine delivered immediately after induction of ischemia (2) 20 mg/kg/day memantiote delivered by osmotic pump starting immediately after induction of ischemia and a 10 mg/kg bolus of memantine delivered at 0.5 and 4.5 hours after reperfusion by intraperitoneal (IP) injection, (3) 20 mg/kg/day memantine delivered by osmotic pump starting immediately after induction of ischemia and a 10 mg/kg bolus of memantine delivered at 3.5 and 7.5 hours after reperfusion by intraperitoneal (IP) injection, or (4) saline (vehicle) alone, delivered by osmotic pump starting 2 days before induction of ischemia, as a control. Ischemic damage was assessed 14 days after induction of ischemia, and the percentage of surviving neurons in the ganglion cell layer was 33 3%, 61 5%, 52 5% and 48 5%, for treatments (1) through (4), respectively. [Lagreze, et al., *Vis. Sci.*, 39:1063–1066 (1998)].

Three fenamates, mefenamate, meclofenamate, and flufenamate were shown to have a protective effect on neurons under ischemic (glucose/oxygen deprivation) or excitotoxic conditions using the isolated retinas of chick embryos as a model. Retinal damage due to ischemic or excitotoxic injury was reduced by exposure to mefenamate, meclofenamate or flufenamnate, as evaluated by lactate dehydrogenase (LDH) release and histological assessment of neuronal cell injury by phase-contrast microscopy. In addition, whole cell recordings indicated that mefenamate, meclofenamate and flufenamate inhibited NMDA receptor mediated currents. [Chen, et al., *Neurosci. Lett.* 242(3):163–166 (1998)]

3. Myocardial Infarction

Animal models of myocardial infarction are well known in the art. Any of a number of models can be used to validate the efficacy of candidate compounds as identified herein. For example, in situ coronary artery occlusion followed by reperfusion in rabbits or dogs is used to assess compounds, where extent of damage to the heart is measured by any of a number of methods, such as magnetic resonance imaging (see, e.g., Kim, R. J., et al., Circulation 100(2) 185–192, 1999; Pislaru, S. V., et al., Circulation 99(5): 690–696, 1999; Schwartz, P. J., Am. J. Cardiol. 81(6A): 14D–20D, 1999).

In vitro to In vivo Correlation

The biological activity of test compounds which have been determined to have efficacy in substantially reducing cell death in excitable cells such as RGCs or myocytes following oxygen/glucose deprivation in vitro may be confirmed in vivo. In vitro efficacy of one or more test compounds in reducing cell death in oxygen/glucose-deprived RGCs requires that the percentage of dead cells in test cultures is substantially less at a selected time after OGD than that of oxygen/glucose-deprived control cultures of RGCs which have not been treated with the one or more test compounds. The test compounds determined to be efficacious in substantially reducing cell death in in vitro oxygen/glucose-deprived RGCs by at least 50%, preferably 75%, more preferably 85% and even more preferably 95–98% relative to untreated control RGCs, are candidates for confirmatory testing in established in vivo animal models for ischemia.

A determination of in vivo activity in animal models for a given compound may be predictive of the biological activity of a structurally related class of compounds such as compounds with the same functional groups, chemical analogs of a basic compound or amino acid or nucleic acid sequence variants.

4. In vitro to In vivo Correlations

As demonstrated by the studies described herein, in vitro assays of the present invention are highly predictive of in vivo efficacy in standard experimental animal models of ischemia. For example, the performance of SNX-111 in the RCG OGD assay was predictive of its neuroprotective effects in various in vivo models of cerebral ischemia.

The biological activity of test compounds that have been determined to have efficacy in substantially reducing cell death in RGCs following growth factor deprivation in vitro may be confirmed in vivo. In vitro efficacy of one or more test compounds in reducing cell death in growth factor-deprived RGCs requires that the percentage of dead cells in test cultures is substantially less at a selected time after GFD than that of growth factor-deprived control cultures of RGCs which have not been treated with the one or more test compounds. The test compounds determined to be efficacious in substantially reducing cell death in in vitro growth factor-deprived RGCs by at least 50%, preferably 75%, more preferably 85% and even more preferably 95–98%, relative to untreated control RGCs, are candidates for confirmatory testing in established in vivo animal models for glaucoma.

A determination of in vivo activity in animal models for a given compound may be predictive of the biological activity of a structurally related class of compounds such as compounds with the same functional groups, chemical analogs of a basic compound or amino acid or nucleic acid sequence variants.

V. Test Compounds

Methods of the present invention are not limited by the choice of compound employed therein. This section provides guidance for pre-selecting compounds for testing in the assays of the invention.

Test compounds for evaluation in the in vitro OGD retinal ganglion cell model encompass numerous chemical classes, though typically they are organic molecules, preferably small organic compounds having a molecular weight of more than 100 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof. Peptides may be candidate compounds; however, non-peptide compounds may have additional advantages with respect to their pharmacokinetic properties.

Large numbers of non-peptide small molecules may be obtained by screening one or more small molecule combinatorial libraries now available.

Test compounds may be selected from one or more of the following categories: a compound effective to interfere with apoptotic or necrotic cell death, e.g. a non-peptide calcium channel blocker, a conopeptide, an NMDA receptor antagonist, a caspase inhibitor, kinase inhibitor, phosphatase inhibitor, compounds that block activation, translocation of death-inducing proteins, etc.

Co-pending U.S. provisional patent applications No. 60/137,618, filed Jun. 4, 1999 and No. 60/138,855, filed Jun. 11, 1999, incorporated herein by reference, describe certain bis-benzimidazole compound families that are a rich source of test compounds in accordance with the present invention. As described therein, these compounds exhibit neuroprotective properties.

Test compounds are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological compounds may be subjected to directed or random chemical modifications, such as acylation, alkylation, esterification, amidification, etc. to produce structural analogs.

The test compounds may also be proteins. By "protein" herein is meant at least two covalently attached amino acids, which includes proteins, polypeptides, oligopeptides and peptides. A peptide, may be one of a plurality of such peptides in a peptide combinatorial library. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. If non-naturally occurring side chains are used, non-amino acid substituents may be used, for example to prevent or retard in vivo degradation.

In another preferred aspect, the test compounds are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening for the ability to reduce the percentage of cell death in an in vitro model for ischemia-related cellular damage. Particularly preferred are libraries of bacterial, fungal, viral, and mammalian proteins, with the latter being preferred, and human proteins being especially preferred.

The test compounds may be peptides of from about 2 to about 30 amino acids, with from about 2 to about 20 amino acids being preferred, and from about 2 to about 15 being particularly preferred. The peptides may be digests of naturally occurring proteins as is outlined above, random peptides, or "biased" random peptides, such as may be produced by a phage display library. See, e.g., Devlin, WO 91/18980; Key, B. K., et al., eds., Phage Display of Peptides and Proteins, A Laboratory Manual, Academic Press, San Diego, Calif., 1996, incorporated herein by reference. Phage display is a powerful technology that allows one to use phage genetics to select and amplify peptides or proteins of desired characteristics from libraries containing $10^8$–$10^9$ different sequences. Libraries can be designed for selected variegation of an amino acid sequence at desired positions, allowing bias of the library toward desired characteristics. Libraries are designed so that peptides are expressed fused to proteins that are displayed on the surface of the bacteriophage. The phage displaying peptides of the desired characteristics are selected and can be regrown for expansion. Since the peptides are amplified by propagation of the phage, the DNA from the selected phage can be readily sequenced facilitating rapid analyses of the selected peptides.

For example, the peptide substrate library containing $10^8$ different sequences is fused to a protein (such as a gene III protein) expressed on the surface of the phage and a sequence that can be used for binding, such as biotin. The phage are digested with protease, and undigested phage are removed by binding to appropriate immobilized binding protein, such as streptavidin. This selection is repeated until a population of phage encoding substrate peptide sequences is recovered. The DNA in the phage is sequenced to yield the substrate sequences. These substrates are then used for further development of peptidomimetics, particularly peptidomimetics having inhibitory properties.

Such peptides can be "randomized" meaning that the peptide consists of essentially random amino acids. Since generally these random peptides are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized test proteinaceous compounds.

The library may be fully randomized, with no sequence preferences or constants at any position. Alternatively, the library is biased. That is, some positions within the sequence are either held constant, or are selected from a limited number of possibilities. For example, nucleotides or amino acid residues may be randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

The test compounds may be nucleic acids. By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones [see, e.g., Eghohm, *J. Am. Chem. Soc.* 114:1895 (1992); Meier, et al., *Chem. Int. Ed. Engl.* 31:1008 (1992); Nielsen, *Nature* 365:566 (1993); Carlsson, et al., *Nature* 380:207 (1996), all of which are incorporated by reference]. Modifications of the ribose-phosphate backbone may be done to facilitate the addition of additional moieties such as labels, or to increase the stability and half-life of such molecules in physiological environments.

In addition, mixtures of naturally occurring nucleic acids and analogs can be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xanthine, hypoxanthine, isocytosine, isoguanine, etc.

As described above generally for proteins, nucleic acid test compounds may be naturally occurring nucleic acids, random nucleic acids, or "biased" random nucleic acids. For example, digests of procaryotic or eucaryotic genomes may be used as is outlined above for proteins. In one aspect, the test compounds are organic chemical moieties, a wide variety of which are available in the literature.

The test compounds may also be "variants" of a compound determined to be biologically active in the test methods of the present invention. For example, a "variant" polynucleotide sequence may encode a "variant" amino acid sequence which is altered by one or more amino acids from the reference polypeptide sequence. The variant polynucleotide sequence may encode a variant amino acid sequence which contains "conservative" substitutions, wherein the substituted amino acid has structural or chemical properties similar to the amino acid which it replaces. In addition, or alternatively, the variant polynucleotide sequence may encode a variant amino acid sequence which contains "non-conservative" substitutions, wherein the substituted amino acid has dissimilar structural or chemical properties to the amino acid which it replaces. Variant polynucleotides may also encode variant amino acid sequences which contain amino acid insertions or deletions, or both. Furthermore, a variant polynucleotide may encode the same polypeptide as the reference polynucleotide sequence but, due to the degeneracy of the genetic code, has a polynucleotide sequence which is altered by one or more bases from the reference polynucleotide sequence.

VI. Treatment Methods

Candidate compounds that have been selected by in vitro activity in the cell culture models for ischemia as described herein are useful for in vivo treatment of ischemia-related cellular damage in a human subject. According to one aspect of the invention, the in vitro properties are used to select and identify candidate compounds which may be efficacious in the in vivo treatment method of the invention. Further screening in appropriate animal models, such as one or more of the models described herein, may also be appropriate, in order to better determine approximate dosages, identify any potential side-effects, and the like. Persons skilled in the art will recognize and use animal models that are appropriate to the particular therapeutic indication for which regulatory approval is to be sought.

For example, candidate compounds that provide protection in the RCG assay described herein are useful in treating or preventing ischemic neuronal damage. Accordingly, the invention provides a treatment method for reducing cellular damage related to an ischemic condition in a human subject. The ischemic condition may be due to an interruption in cerebral circulation, such as caused by cardiac failure, or other condition leading to global loss of blood supply to the brain, or due to localized interruptions in blood flow, such as due to cerebral hemorrhaging, or localized thrombotic or embolic events, or head trauma (i.e. global or focal ischemia). Alternatively, the damage may be to myocardial tissue, as resulting from decreased perfusion of the coronary arteries (heart attack).

Neuronal cell damage following an ischemic event resulting from the sudden diminution or loss of neurological function caused by a decrease in or loss of blood supply, is often accompanied by secondary damage resulting from the original ischemic event. The secondary damage typically includes cerebral cell destruction, or lesions, in the area surrounding the ischemic injury, in the case of focal ischemia, and also in areas of selective vulnerability in lesions, such as the hippocampus or basal ganglia, in the case of global ischemia. The treatment method of the invention is effective in reducing or preventing both anatomical and functional secondary damage related to ischemia.

Compounds that are therapeutically effective in the methods of the present invention are able to modulate the cell death associated with ischemic injury. The compounds having the desired therapeutic effect may be administered in a physiologically acceptable carrier to a host. The agents may be administered in a variety of ways, e.g., orally, parenterally subcutaneously, intraperitoneally, intravascularly, etc. The compounds may be formulated in a variety of ways, depending upon the manner of introduction. For example, a candidate compound is formulated for parenteral administration in a suitable inert carrier, such as a sterile physiological saline solution. For example, if the compound is a peptide, the concentration of peptide in the carrier solution is typically between about 0.1–10 mg/ml. The dose administered will be determined by route of administration. For example, for preventing central neuronal damage, particularly when conopeptides such as SNX-111 are employed, a suitable route is intracerebroventricular (IC), at a dose level of about 1–500 mg peptide/kg body weight, depending on the effective concentration of the peptide.

A therapeutically effective dose and route of administration, i.e., a dose effective to produce a significant reduction in the anatomical and/or functional cellular damage resulting from ischemia can be estimated as noted above, from the effective concentrations observed in the in vitro retinal ganglion cell culture method of the present invention and validated, for example, in the gerbil and rat animal models for ischemia, as described herein. The dose level can also be estimated, for new compounds, by comparison with established effective doses for known compounds with structural similarities, or by comparison with unrelated compounds, taking into consideration predicted variations in bioavailability, biodistribution and other pharmacokinetic properties, as can be empirically determined by persons skilled in the art. Such approximate dosages can also be corrected for observed differences in the activity in vitro assay of oxygen/glucose-deprived cells.

The candidate compound may be administered prior exposure to an event likely to expose a subject to neuronal ischemia, such as prior to open heart surgery, which has associated with it a high incidence of thromboembolytic stroke. Compound may also be administered during any such event, or immediately thereafter, to prevent further neuronal damage, such as delayed damage that occurs in the hours or days following cerebral ischemia. Further, it has been observed that certain compounds, for example, the conopeptide SNX-111 are protective, even when administered at various times after the onset of the ischemic event, e.g., any time up to about 24 hours, or even longer, following the period of transient occlusion (e.g., U.S. Pat. No. 5,559,095, incorporated herein by reference). The delayed-administration protective effect indicates that the test compound is effective in blocking the events leading from ischemic injury to secondary cerebral injury, which events may occur over a period of many hours or even days after injury. Thus, the delayed administration may be effective to reduce secondary cerebral damage over a time period of from one to several hours, or even a day or more, following the onset of ischemia.

The therapeutically effective amount of a test compound can be provided in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Therapeutic compositions containing candidate compounds may contain additional additives as appropriate, for securing an adequate pH value, and facilitating effective administration.

In summary, the therapeutically effective amount of a test compound can be estimated based on the concentration effective to reduce cell death in vitro in retinal ganglion cells subjected to an ischemic challenge.

The following examples serve to more fully describe the manner of using the above-described invention, as well as to set forth the best modes for carrying out various aspects of the invention. It is understood that these examples in no way serve to limit the true scope of this invention, but rather are presented for illustrative purposes. All references cited herein are incorporated by reference.

EXAMPLE 1
Purification and Culture of Retinal Ganglion Cells
A. Isolation of Retinal Ganglion Cells Using sequential immunopanning, RGCs can be purified to greater than 99% homogeneity. Typically, 20–30% of the RGCs are isolated, which is about 40,000 to 60,000 RGCs per P8 (post-natal, day 8) animal.

The tissue from P8 Sprague/Dawley rat retinas (Simonsen Labs, Gilroy, Calif.) was dissociated enzymatically to obtain a suspension of single cells, by incubating the tissue in a papain solution (15 U/ml per retina, Worthington) in Earle's balanced salt solution (EBSS, Gibco) containing L-cysteine at 37 C. for an appropriate time to dissociate the tissue. The tissue was then disrupted sequentially with a 1 ml pipette, in a solution containing ovomucoid (Boehringer-Mannheim, Indianapolis, Ind.), DNase (Sigma), and bovine serum albumin (BSA; Sigma) to yield a single cell suspension. The cells were then washed in a suspension of ovomucoid/BSA.
B. Panning Procedure Panning plates were prepared in petri dishes (150 mm for the anti-rabbit IgG plates and 100 mm for the T11D7 plate) by incubating with Tris buffer solution (pH 9.5) containing 10 mg/ml of secondary antibody for approximately 12 hours at 4 C. Either affinity-purified goat anti-rabbit IgG (H+L chain-specific; Jackson Laboratories, Bar Harbor, Me.) or affinity-purified goat anti-mouse IgM (mu chain-specific; Jackson Laboratories) was used as the secondary antibody. The plates were then washed three times with phosphate-buffered saline (PBS) and the dish with anti-mouse IgM antibodies is further incubated with Thy 1.1 IgM monoclonal supernatant (antibody against mouse Thy 1.1, T11D7e2, ATCC, TIB 103) for approximately 2 hours at room temperature. After removing the supernatant, the plate was washed three times with PBS. To prevent non-specific binding of cells to the panning dish, PBS containing 2 mg/ml bovine serum albumin (BSA) was placed on the panning dishes.

The retinal cell suspension was incubated with anti-rat macrophage antiserum (Axell) for approximately 20 minutes, centrifuged, resuspended in PBS and incubated on an anti-rabbit panning plate for approximately 45 minutes. The plate was gently swirled every 15 minutes to ensure access of all cells to the surface of the plate. Following this, the cell suspension was transferred to a second anti-rabbit panning plate for approximately 30 minutes. Non-adherent cells were removed with the supernatant, filtered through a 15 mm Nytex mesh (Tetko) and placed on the T11D7 panning plate. After approximately 45 minutes, the plates were washed eight times with PBS to remove the non-adherent cells.
C. Removing Adherent Cells from the Plate Four ml of a trypsin solution (0.125%) was prepared by diluting a trypsin stock (Sigma) in EBSS (Ca and Mg free Eagle's balanced salt solution). The cells in the panning dish were incubated with this solution for ten minutes in a 5% $CO_2$ incubator. The cells were dislodged by gently pipetting the trypsin solution across the plate. Ten ml of the 25% fetal calf serum was added to inactivate the trypsin and the cells were centrifuged and resuspended in culture medium.
D. Culture of Retinal Ganglion Cells Approximately 5,000 purified RGCs were cultured in 96-well plates (Falcon Labware, Oxnard, Calif.), precoated with poly-D-lysine (PDL, 70 kD, 10 mg/ml; Sigma) and merosin (2 mg/ml; Gibco). The RGCs were cultured in serum-free Neurobasal medium [Brewer, et al., *J. Neurosci. Res.* 35:567–576 (1993), Gibco] containing Sato-Bottenstein and B27 (Gibco) supplement, insulin (Sigma, 5 mg/ml), brain-derived neurotrophic factor (BDNF, 25 ng/ml; Preprotech), ciliary neurotrophic factor (CNTF, 20 ng/ml; Preprotech) and forskolin (10 mM, Sigma). The percentage of surviving cells was assessed at 3, 7, and 14 days by the MTT assay (see below).

Figure 2A:
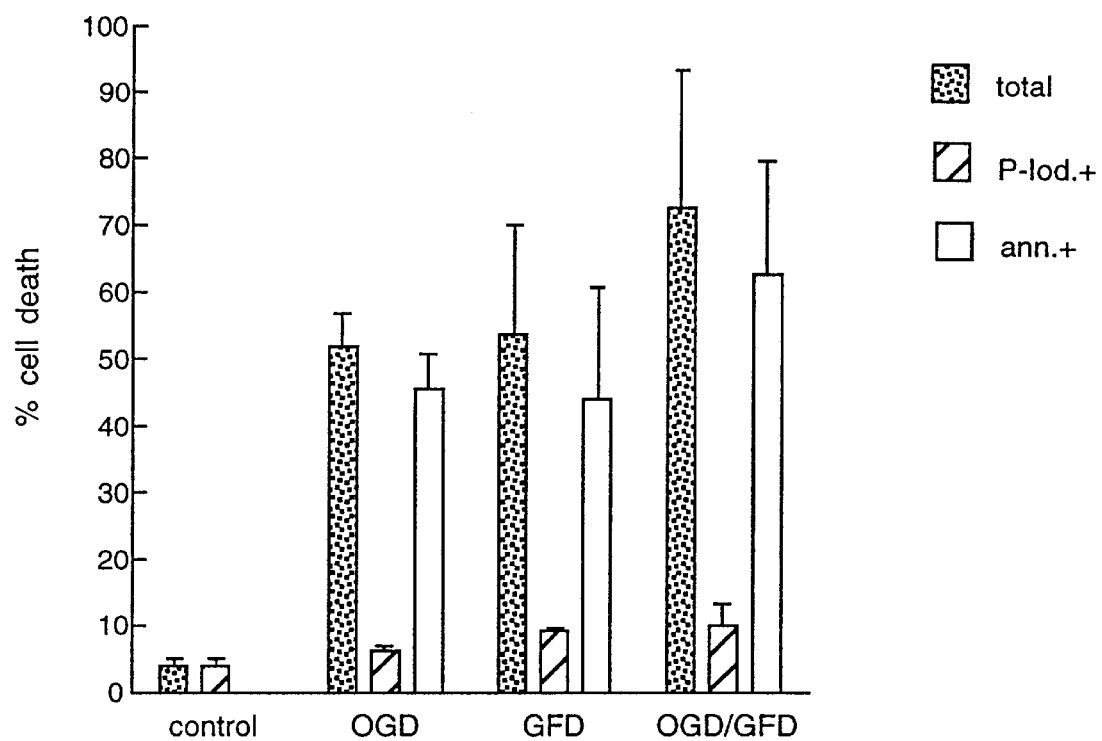
FIGS. 2A and B show the percentage of cell death of retinal ganglion cells 24 hours (2A) and 48 hours (2B) after oxygen/glucose deprivation (OGD), growth factor deprivation (GFD) or OGD plus GFD, as determined by propidium iodide and annexin assay (ApoAlert Kit, Clontech).
Figure 2B:
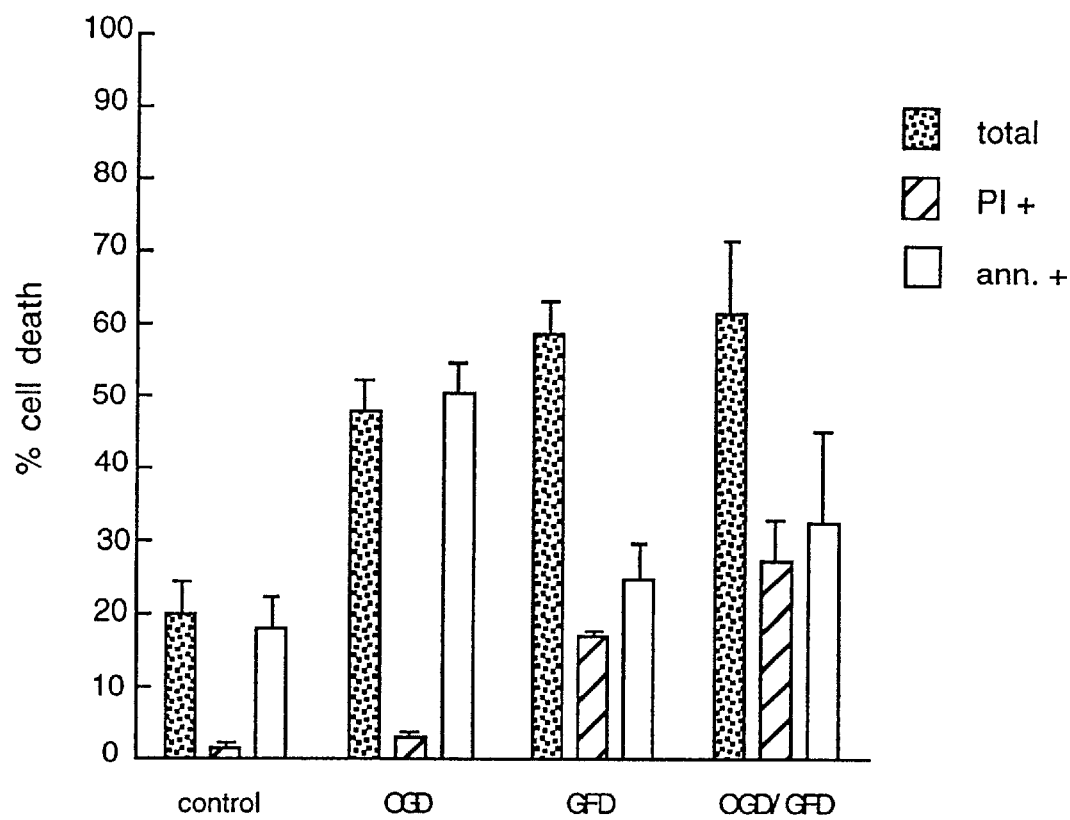

EXAMPLE 2
Evaluation of Test Compounds in an In vitro Ischemia Model
A. Oxygen/Glucose Deprivation Model for Ischemia Retinal ganglion cells were grown in 96-well plates for 5 days in serum-free medium as described above. On the sixth day cells were washed three times in a salt solution, e.g. Earle's balanced salt solution (EBSS, Gibco), containing glucose for control cells, and lacking glucose for test cells (oxygen/glucose-deprived cells). Control cells were further incubated in a 5% $CO_2$ incubator while OGD cells were deprived of oxygen in an anaerobic chamber (for 3 hours). After 3 hours, control and test cells were washed once with glucose-containing salt solution and cultured an additional 48 hours in serum-free neurobasal medium containing factors as described above in a 5% $CO_2$ incubator, followed by a determination of cell viability using three different cell death assays; MTT, propidium iodide and annexin assays.
B. Effect of Oxygen/Glucose Deprivation on RGCs 24 hours after oxygen/glucose deprivation (OGD), approximately 25% less retinal ganglion cells were determined to be alive relative to non-deprived control cells. After 48 hours 40% less cells survived relative to non-deprived control cells (see FIG. 1). The dead cells showed the typical shrunken morphology of apoptotic cells. To confirm that the retinal ganglion cells died of programmed cell death (apoptosis) following OGD, cell cultures were labeled with FITC-coupled annexin V (ApoAlert Kit, Clonetech) and PI at 24 and 48 hours after OGD, followed by light and fluorescent microscopy. 200 cells were counted per triplicate value. The percentage of annexin-positive cells was consistent with that of dead cells observed in previous experiments (see FIG. 2). Approximately 80% of total dead RGCs were also annexin V positive at both 24 and 48 hours, indicating that the majority of cells died by apoptosis (FIGS. 2A and 2B).

C. Effect of SNX-194 on Oxygen Glucose Deprived RGCs

The N-calcium channel blocker, omega-conopeptide analog, SNX-194 (which represents a single amino acid change from SNX-111), was added to control cells and cells deprived of oxygen and glucose 30 minutes prior to OGD, during OGD and for 24 to 48 hours after OGD. RGCs were protected from apoptotic cell death by SNX-194 in a dose dependent manner, with an optimal concentration of 1–10 nM which saved 90–100% of the RGCs (see FIG. 3). A non-active control peptide, termed herein, SNX-444, did not show any protection in this assay even when tested at a concentration 100 that of the test peptide SNX-194, (i.e. 10 M versus 100 nM) (see FIG. 4). Thus it can be concluded that the evaluation of apoptotic cell death in the retinal ganglion cell assays of the present invention can be used to differentiate the specific protective effects of various peptides or other test compounds from test compounds that are not protective.

D. SNX-230 and Nitrendipine Partially Protect RGCs from Apoptosis after OGD

In order to determine whether blockers of various calcium channel types can protect RGCs from ischemia-induced apoptosis, a synthetic omega-conopeptide-like molecule, SNX-230, was evaluated for its ability to protect OGD retinal ganglion cells from apoptotic cell death in vitro, as described above for SNX-194. SNX-230, a P/Q type specific inhibitor, had little protective effect, which can be explained by the fact that RGCs may express low numbers of P/Q-type calcium channels. Nitrendipine, an L-type calcium channel blocker, was also tested and showed protection from OGD-induced apoptosis, but to a lesser extent than SNX-194 (FIG. 5).

E. Effect of NMDA Receptor Antagonists on Oxygen/Glucose Deprived RGCs

In order to determine whether NMDA receptor antagonists can protect RGCs from ischemia-induced apoptosis, RGCs were treated with various NMDA receptor antagonists beginning 30 minutes prior to OGD and continuing for up to 48 hours after OGD, as compared to untreated and non-oxygen glucose deprived control cells. Compounds that were tested for their ability to modulate the effect of oxygen/glucose deprivation on retinal ganglion cells include mefenamic acid, meclofenamic acid, flufenamic acid, DL-2-amino-5-phosphonovaleric acid (AP-5), and DL-2-amino-7-phosphonovaleric acid (AP-7), at concentrations of 0, 1, 10 and 100 $\mu$M, respectively.

Figure 6:
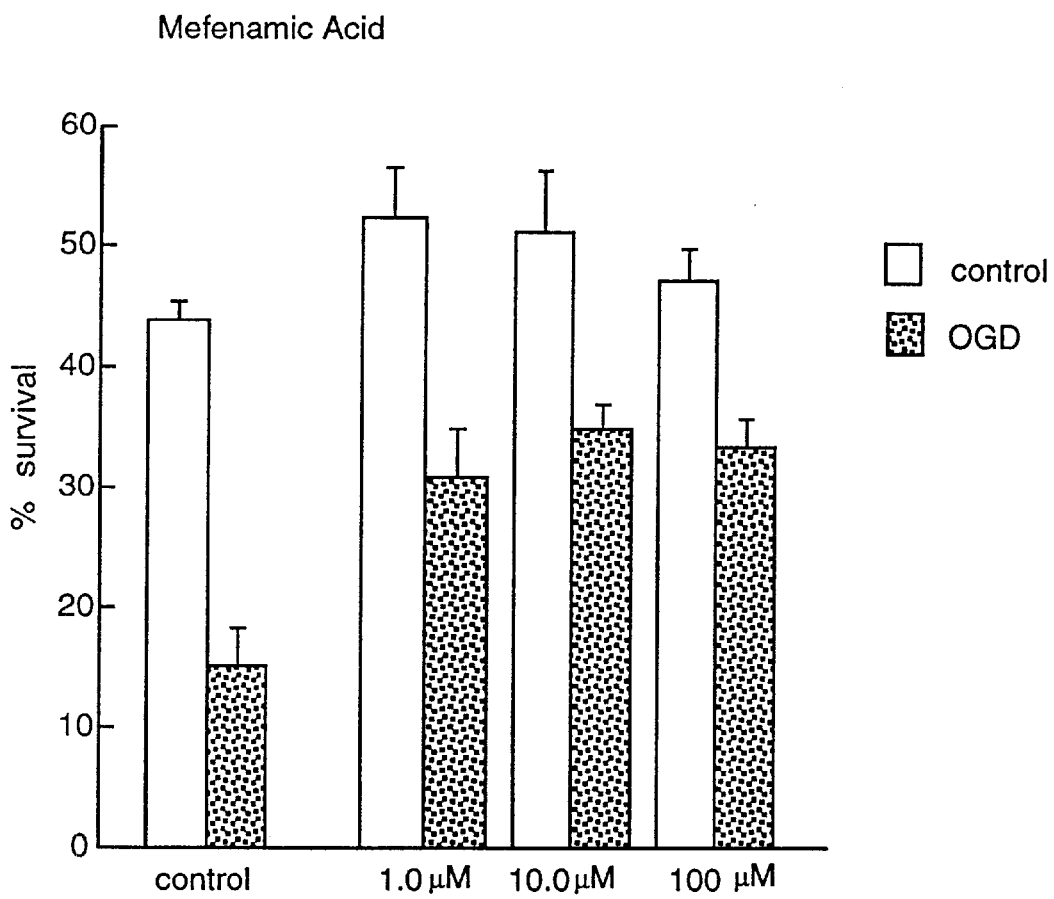
FIG. 6 shows the effect of pre-treatment of retinal ganglion cells with mefenamic acid, beginning 30 minutes prior to OGD and continuing for up to 48 hours after OGD, as indicated by the percentage survival of retinal ganglion cells at 48 hours after oxygen/glucose deprivation (OGD). Black bars indicate the percentage survival of non-oxygen glucose deprived control cells in the presence of 0, 1, 10 or 100 µM of mefenamic acid. Striped bars indicate the percentage survival of oxygen glucose deprived control cells in the presence of 0, 1, 10 or 100 µM of mefenamic acid.
Figure 7:
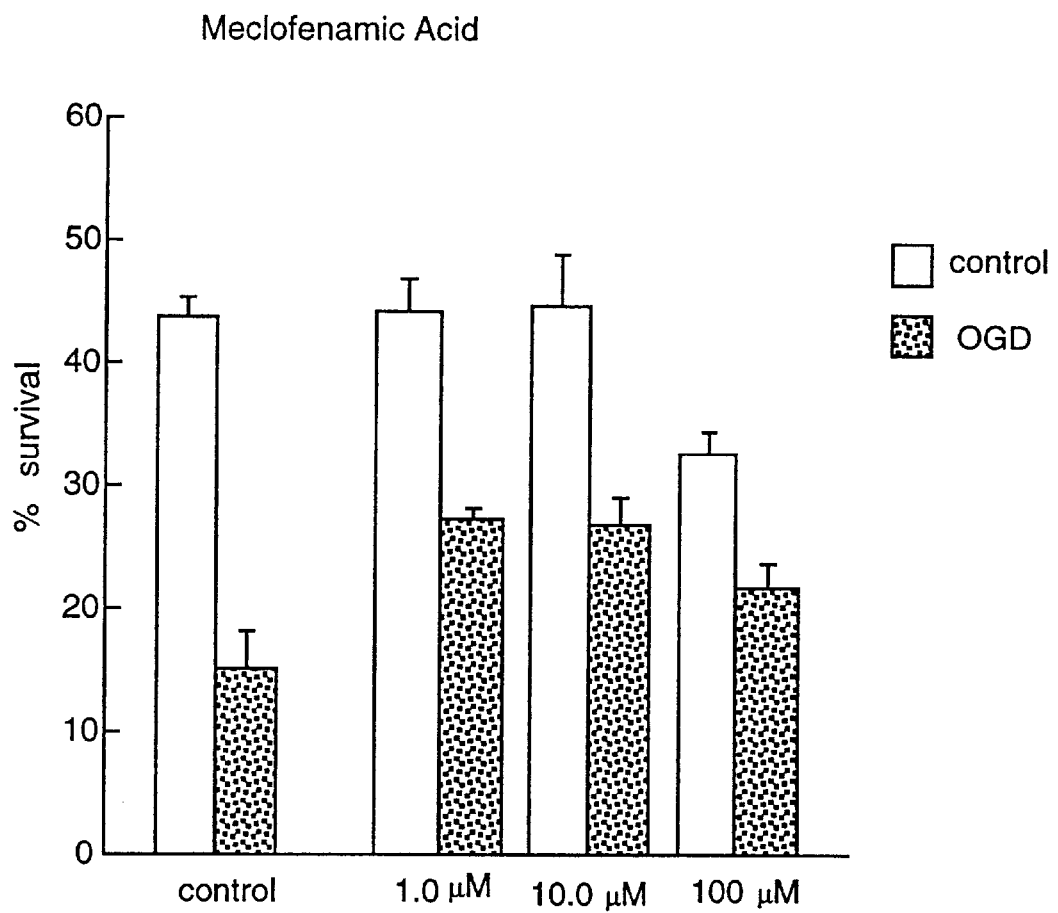
FIG. 7 shows the effect of pre-treatment of retinal ganglion cells with meclofenamic acid, beginning 30 minutes prior to OGD and continuing for up to 48 hours after OGD, as indicated by the percentage survival of retinal ganglion cells at 48 hours after oxygen/glucose deprivation (OGD). Black bars indicate the percentage survival of non-oxygen glucose deprived control cells in the presence of 0, 1, 10 or 100 µM of meclofenamic acid. Striped bars indicate the percentage survival of oxygen glucose deprived control cells in the presence of 0, 1, 10 or 100 µM of meclofenamic acid.
Figure 8:
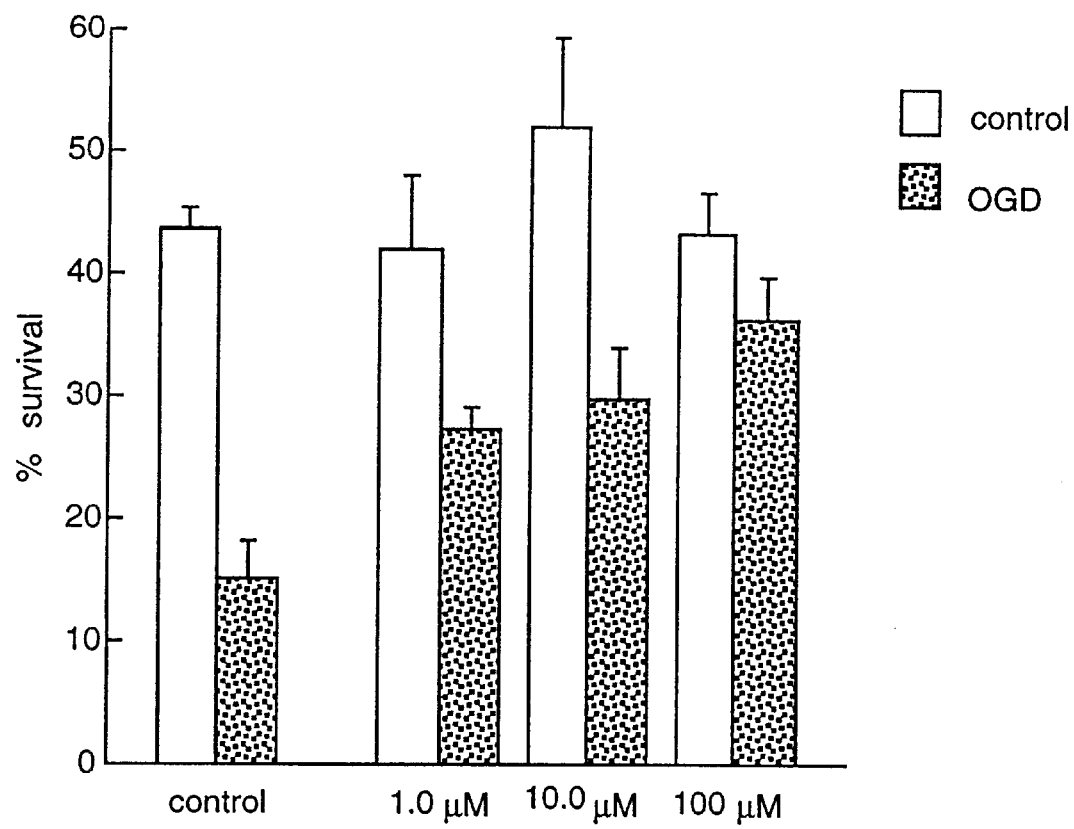
FIG. 8 shows the effect of pre-treatment of retinal ganglion cells with flufenamic acid, beginning 30 minutes prior to OGD and continuing for up to 48 hours after OGD, as indicated by the percentage survival of retinal ganglion cells at 48 hours after oxygen/glucose deprivation (OGD). Black bars indicate the percentage survival of non-oxygen glucose deprived control cells in the presence of 0, 1, 10 or 100 µM of flufenamic acid. Striped bars indicate the percentage survival of oxygen glucose deprived control cells in the presence of 0, 1, 10 or 100 µM of flufenamic acid.
Figure 9:
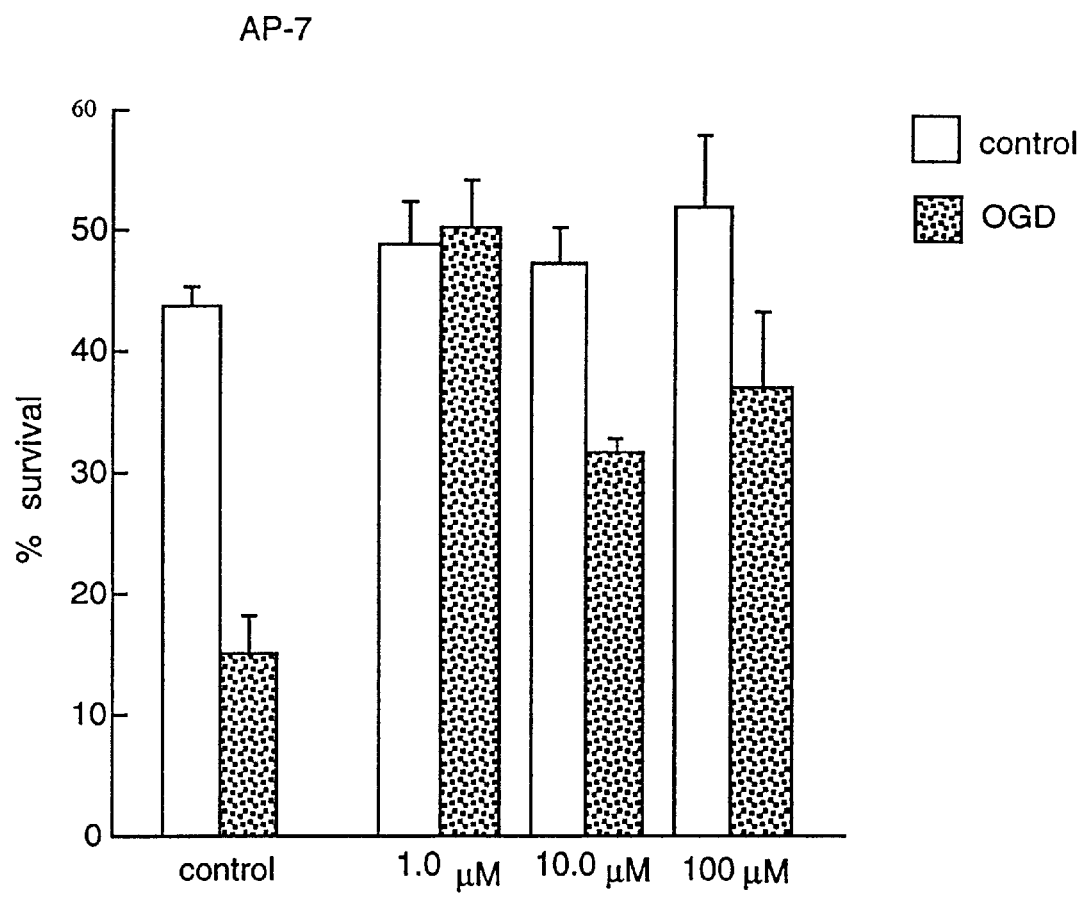
FIG. 9 shows the effect of pre-treatment of retinal ganglion cells with DL-2-amino-7-phosphono-valeric acid (AP-7), beginning 30 minutes prior to OGD and continuing for up to 48 hours after OGD, as indicated by the percentage survival of retinal ganglion cells at 48 hours after oxygen/glucose deprivation (OGD). Black bars indicate the percentage survival of non-oxygen glucose deprived control cells in the presence of 0, 1, 10 or 100 µM of DL-2-amino-7-phosphonovaleric acid (AP-7). Striped bars indicate the percentage survival of oxygen glucose deprived control cells in the presence of 0, 1, 10 or 100 µM of DL-2-amino-7-phosphono-valeric acid (AP-7).
Figure 10:
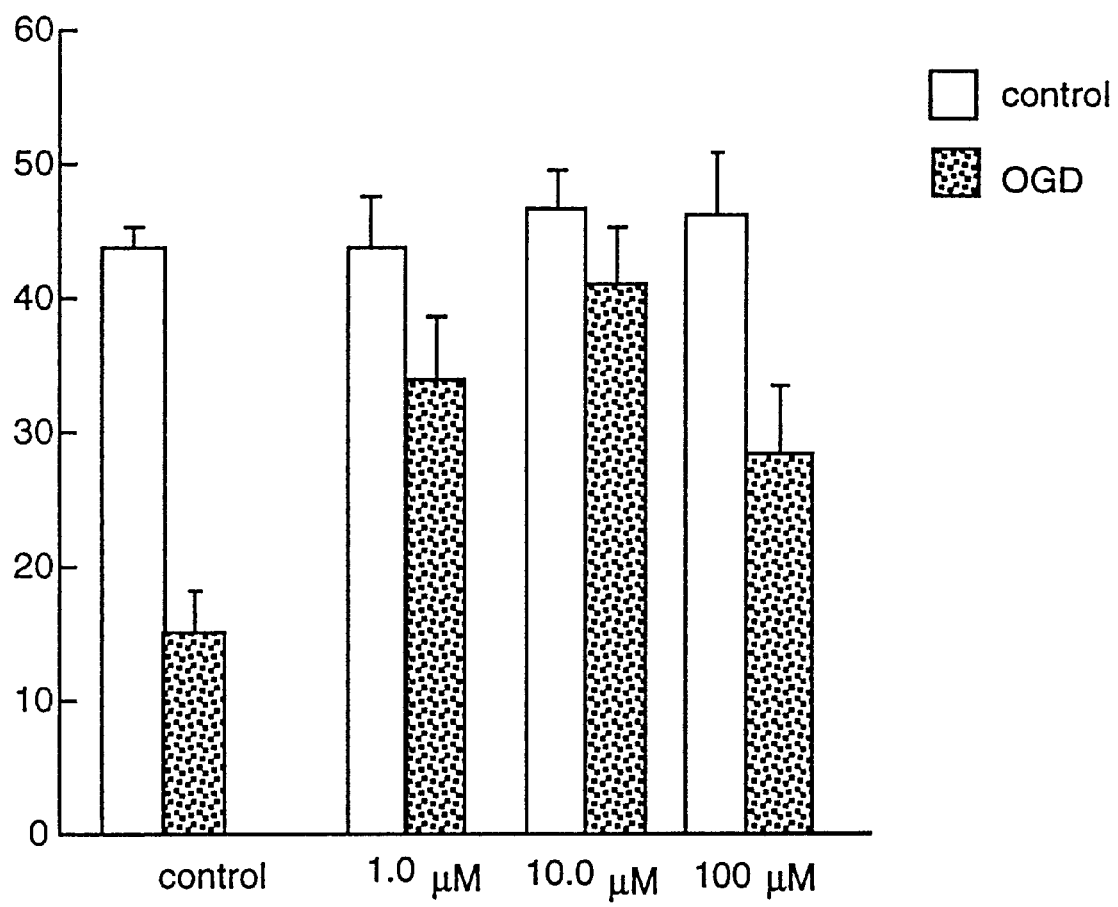
FIG. 10 shows the effect of pre-treatment of retinal ganglion cells with DL-2-amino-5-phosphonovaleric acid (AP-5), beginning 30 minutes prior to OGD and continuing for up to 48 hours after OGD, as indicated by the percentage survival of retinal ganglion cells at 48 hours after oxygen/glucose deprivation (OGD). Black bars indicate the percentage survival of non-oxygen glucose deprived control cells in the presence of 0, 1, 10 or 100 µM of DL-2-amino-5-phosphonovaleric acid (AP-5). Striped bars indicate the percentage survival of oxygen glucose deprived control cells in the presence of 0, 1, 10 or 100 µM of DL-2-amino-5-phosphono-valeric acid (AP-5).

Protection from OGD-induced apoptosis was observed following treatment with AP-5, AP-7 and flufenamic acid with approximately 30% or greater survival of RGCs observed at concentrations of 1, 10 and 100 $\mu$M relative to approximately 15% survival for untreated OGD control cells. (FIGS. 8–10) Less efficacy was observed following treatment with mefenamic acid and meclofenamic acid (FIGS. 6–7).

EXAMPLE 3

Evaluation of Test Compounds in an in vivo Global Ischemia Model

A. Gerbil Model

Global ischemic damage was examined in the gerbil model, according to standard procedures (Kirino). Male Mongolian gerbils (*Meriones unguiculatus*, Tumblebrook Farm, West Brookfield, Mass.) weighing 50–80 g were anesthetized in a small chamber with 4% halothane carried by 70% nitrous oxide (0.44 L/min) and 30% oxygen (0.19 L/min). Using aseptic techniques, both common carotid arteries were exposed, dissected free of surrounding tissue, and occluded with microvascular clamps approximately 3 to 4 mm above the clavicle. The occlusions were maintained for 8 minutes.

During or after the occlusion, an intracerebroventricular (IC) injection aimed at the lateral ventricle was accomplished using a 10 $\mu$l Hamilton syringe with a 27 gauge needle for injection of drug. Occluded animals received either drug or its vehicle. Injected, unoccluded controls were anesthetized, and received the IC injection only.

Twenty-four to seventy-two hours following occlusion the animals were evaluated for brain damage. This was accomplished by anesthetizing the animals, followed by perfusion first with PBS containing heparin, then with 10 ml of Zamboni's fix 15% (vol/vol) picric acid 4% (wt/vol) paraformaldehyde in 0.1 M phosphate buffer pH 7.4. Brains were removed and left immersed in the same fixative for several hours.

Brain hippocampal sections were collected, stained with haematoxylin and eosin, essentially as to reported in the literature. Cells in the drug-treated ischemic animals appeared normal microscopically, whereas damage was apparent in the ischemic animals receiving vehicle alone The extent of anatomical damage in ischemic animals treated with 0.1 $\mu$g of SNX-111 at the time of the ischemic event was only 25% of that seen in untreated animals. When 0.1 $\mu$g of SNX-111 was administered per animal by IC infusion 1 hour following the 8 minute occlusion, the extent of anatomical damage in ischemic animals was only 30% of that seen in untreated animals, indicating little loss of protection when the drug is administered 1 hour post-occlusion.

B. Rat Model

Global ischemic damage was examined in the rat brain model, employing the four-vessel occlusion method of Pulsinelli, et al., 1979. Surgery was performed to permanently occlude both vertebral arteries and to implant an arterial clasp to allow temporary occlusion of the carotid arteries at a later time. Under sodium pentobarbital anesthesia (60 mg/kg) male Fisher 344 rats were placed in a stereotaxic holder and the first cervical vertebra was exposed with the aid of a dissecting microscope. The vertebral arteries were occluded with a thermocautery device and the skin closed with wound clips. The animal was placed on its back and the carotid arteries were carefully dissected free of the surrounding nerves and vessels under the microscope, clasps were inserted and tied into the skin so as to externalize the ends of the loop. Ischemia in the rat model system was induced by first surgically closing the vertebral arteries, and after surgical recovery, transiently blocking the carotid arteries (by tightening clasps and completely blocking blood flow to the brain) for a period of 15 minutes. During occlusion, animals were given 0.3 $\mu$g SNX-111 IC per animal. Four days after occlusion, the animals were examined histologically, to determine the extent of damage in the hippocampal CA1 region. The extent of damage in treated animals was approximately 30% of that seen in untreated animals. (See also, U.S. Pat. No. 5,051,403).

EXAMPLE 4

Evaluation of Test Compounds in an in vitro Glaucoma Model

A. Growth Factor Deprivation Model for Glaucoma

Retinal ganglion cells were grown in 96-well plates for 5 days in serum-free medium as described above. On the sixth day cells were washed three times in a salt solution, e.g. Earle's balanced salt solution (EBSS, Gibco), containing growth factors for control cells, and lacking growth factors for test cells (oxygen/glucose-deprived cells). Control cells were resuspended and cultured in serum-free medium containing Sato-Bottenstein and B27 supplements, insulin (Sigma), BDNF (PreProtek), CNTF (PreProtek) and forskolin (Sigma). Growth factor-deprived RGCs were resuspended and cultured in serum-free medium containing Sato-Bottenstein and B27 supplements, but lacking insulin, BDNF, CNTF and forskolin. Test and control RGCs were cultured with test compounds for an additional 48 hours in a 5% $CO_2$ incubator, washed three times with glucose containing salt solution and cultured an additional 48 hours in a 5% $CO_2$ incubator, followed by a determination of cell viability using one or more of the MTT, propidium iodide and annexin assays.

B. Effect of Growth Factor Deprivation on RGCs 24 hours after growth factor deprivation (GFD), approximately 40% and 5% less retinal ganglion cells were determined to be alive by Annexin V and PI staining, respectively, relative to non-deprived control cells. 48 hours, after GFD, approximately 7% and 15% less retinal ganglion cells were determined to be alive by Annexin V and PI staining, respectively, relative to non-deprived control cells. The dead cells showed the morphology of apoptotic cells, which was confirmed by staining with FITC-coupled annexin V (ApoAlert Kit, Clonetech) and PI at 24 and 48 hours after GFD and an alysis by FACS with 200 cells counted per triplicate value. Approximately 43 of the 54% and 25 of the 58% total dead RGC were also annexin V positive, at 24 and 48 hours, respectively. (FIGS. 2A and 2B).

EXAMPLE 5

Evaluation of Test Compounds in an in vitro Model of Myocardial Infarction

A. Preparation of Cardiac Myocytes

Heparin (100 units) was administered intraperitoneally to ne day old rat pups, and the hearts were quickly removed into chilled dissociation buffer, as described by Simpson, P. and Savion, S. (1982) Circ. Res. 50, 101–116, incorporated herein by reference. The ventricles were cut into 1–2 mm cubes and were dissociated by alternating treatments at 24° C. with (a) 0.1% trypsin plus 0.002% DNase in dissociation buffer for 5 min at 100 rpm (24 ml spinner flasks) and (b) 2% calf serum indissociation buffer for 1–2 minutes with gentle pipeting.

Cells from the first two combined treatments (a and b) were discarded and the sequence was repeated an additional eight times. Freed cells were collected in cold culture medium with 0.5% calf serum and 0.2% DNase, centrifuged (0° C., 433×g, 10 min), washed in the same medium, strained and incubated in culture medium with 0.5% calf serum in 3×100 mm culture dishes at 37° C. with 1% $CO_2$. The cells were plated for 30 min and the myocytes (unattached cells) were collected and transferred to pre-wetted 35 mm plates in culture medium with 5% calf serum and 0.1 mM BrdU ($4 \times 10^6$ cells/60 mm plate). After 6 hours incubation, the non-attached cells were discarded. Eighteen hours later, the cultures were washed with PBS (pH 7.3) containing 5.5 mM glucose. One milliliter of culture medium (M-199 media) with 10% fetal bovine serum (FBS, Hyclone), 0.1 mM BrdU, 50 units/ml penicillin and 80 $\mu$M vitamin B12 was renewed at this time and every third day thereafter. BrdU was retained in the medium for the first four days in culture. On day four, myocytes were placed in defined medium containing 10 $\mu$g/ml insulin, 10 $\mu$g/ml transferrin, 80 $\mu$M vitamin C, 50 units/ml penicillin and 80$\mu$ Vitamin B12 in M-199 medium.

Experiments were performed on days 5–6. For these experiments, ischemia was induced in a humidified 37° C. incubator within an airtight hypoxia chamber maintained with <0.1% oxygen/1% carbon dioxide and the balance nitrogen. Defined MEM without glucose was equilibrated to low oxygen within the glove box for at least 90 minutes before commencement of the experiment. Inside the glove box, cells were washed twice with warm pre-equilibrated medium before adding incubation medium. For experimental cells, SNX-912 was included in the incubation medium. The cells were incubated in the hypoxic environment for 8 or 16 hours. After the selected time period, the cells were removed from the chamber, washed twice with oxygen- and glucose-containing medium and then incubated with oxygen- and glucose-containing medium at 37° C. in 1% carbon dioxide. The cells were maintained this way for 24 or 48 hours.

After 24 or 48 hours, cell survival was determined with MTT, a yellow tetrazolium salt that can be visualized upon conversion to the blue formazan product. The tetrazolium ring is cleaved by dehydrogenases in active mitochondria; thus, the reaction only occurs in living cells.

Although the invention has been described with respect to particular treatment methods and composition, it will be apparent to those skilled that various changes and modifications can be made without departing from the invention.

What is claimed is:

1. A method of screening test compounds as candidates for treating or preventing ischemia-related cellular damage, comprising subjecting a purified primary culture of at least 75% retinal ganglion cells to an oxygen/glucose deprivation challenge sufficient to produce cell death in at least 25% of the retinal ganglion cells when examined at a selected time after the challenge, exposing said cells to one or more test compounds to be screened, examining the cells at such selected time after challenge for the presence of cell death, and selecting the test compound as a candidate for treating ischemia-related cellular damage if the percentage of dead cells in the test culture is substantially less than that of a control culture.

2. The method of claim 1, wherein said retinal ganglion cells are at least 80% of said purified primary culture.

3. The method of claim 1, wherein said retinal ganglion cells are at least 90% of said purified primary culture.

4. The method of claim 1, wherein said retinal ganglion cells are at least 99% of said purified primary culture.

5. The method of claim 1, wherein said examining is for the presence of apoptotic cell death.

6. The method of claim 1, wherein said examining is for the presence of necrotic cell death.

7. The method of claim 1, wherein said examining is for the presence of non-apoptotic, non-necrotic cell death.

8. The method of claim 1, wherein the test compound is calcium channel blocker.

9. The method of claim 1, wherein the test compound is an N-methyl-D-aspartate (NMDA receptor antagonist.

10. The method of claim 1, wherein the test compound is a bis-benzimidazole.

11. The method of claim 1, wherein said ischemia-related cellular damage is neuronal ischemia.

12. The method of claim 11, wherein said ischemia-related cellular damage is neuronal cell damage in the central nervous system associated with cerebral ischemia.

13. The method of claim 1, wherein the primary culture cells are purified by immunopanning.

* * * * *